(12) United States Patent
Anastassiades

(10) Patent No.: US 10,239,962 B2
(45) Date of Patent: Mar. 26, 2019

(54) HYALURONIC ACID DERIVATIVES

(71) Applicant: Queen's University at Kingston, Kingston (CA)

(72) Inventor: Tassos Anastassiades, Kingston (CA)

(73) Assignee: Queen's University at Kingston, Kingston, ON (CA)

(*) Notice: Subject to any disclaimer, the term of this patent is extended or adjusted under 35 U.S.C. 154(b) by 0 days.

(21) Appl. No.: 15/586,383

(22) Filed: May 4, 2017

(65) Prior Publication Data

US 2018/0051100 A1 Feb. 22, 2018

Related U.S. Application Data

(63) Continuation of application No. 14/209,309, filed on Mar. 13, 2014, now Pat. No. 9,644,040.

(60) Provisional application No. 61/782,298, filed on Mar. 14, 2013.

(51) Int. Cl.
*A61K 8/73* (2006.01)
*C08B 37/08* (2006.01)
*A61K 9/00* (2006.01)
*A61K 31/728* (2006.01)

(52) U.S. Cl.
CPC ........ *C08B 37/0072* (2013.01); *A61K 31/728* (2013.01); *A61K 8/735* (2013.01); *A61K 9/0048* (2013.01); *A61K 9/0051* (2013.01)

(58) Field of Classification Search
CPC ... A61K 8/735; A61K 31/728; C08B 37/0072
See application file for complete search history.

(56) References Cited

U.S. PATENT DOCUMENTS

| 4,810,784 | A | | 3/1989 | Larm | |
|---|---|---|---|---|---|
| 5,728,391 | A | * | 3/1998 | Ikeya | A61K 31/728 424/401 |
| 8,288,129 | B2 | | 10/2012 | Lai et al. | |
| 9,644,040 | B2 | | 5/2017 | Anastassiades | |

FOREIGN PATENT DOCUMENTS

WO WO00/01733 1/2000

OTHER PUBLICATIONS

Ochiai, H., et al., "Bottom-Up Synthesis of Hyaluronan and Its Derivatives via Enzymatic Polymerization: Direct Incorporation of an Amido Functional Group", Biomacromolecules, vol. 6, pp. 1068-1084, (2005).
Medzhitov, R. et al., "A Human Homologue of the *Drosophila* Toll Protein Signals Activation of Adaptive Immunity", Nature, vol. 388, pp. 394-397, (1997).
Lu, Y-C. et al., "LPS/TLR4 Signal Transduction Pathway", Cytokine, vol. 42, pp. 145-151, (2008).
Madhunapantula, S.V., et al., "The Effect of Substitution of the N-acetyl groups of N-acetylgalactosamine Residues in Chondroitin Sulfate on its Degradation by Chondroitinase ABC", Glycoconj J., vol. 24, pp. 465-473, (2007).
Horton, MR et al., "Hyaluronan Fragments synergize with interferon-gamma to induce the C-X-C chemokines mig and interferon-inducible protein-10 in mouse macrophages", J. Biol. Chem. 273(52) 35088-35094, 1998.
Teder, P., et al., "Resolution of Lung Inflammation by CD44", Science, vol. 296: pp. 155-158, (2002).
Yamawaki, H. et al., "Hyaluronan Receptors involved in Cytokine Induction in Monocytes", Glycobiology, vol. 19, No. 1, pp. 83-92, (2009).
Scheibner, K.A., et al., "Hyaluronan Fragments Act as an Endogenous Danger Signal by Engaging TLR2", Journal of Immunology, vol. 177, pp. 1272-1281, (2006).
Crescenzi, V. et al., "NMR Structural Study of Hydrogels Based on Partially Deacetylated Hyaluronan", Macromol. Biosci., vol. 2, pp. 272-279 (2002).
Aziz, M. et al., "Current trends in inflammatory and immunomodulatory mediators in sepsis", Journal of Leukocyte Biology, vol. 93, pp. 329-342, (2013).
Cazzola, M. et al., "Emerging anti-inflammatory strategies for COPD", European Respiratory Journal, vol. 40, No. 3, pp. 724-741, (2012).
Chen, G.Y., et al., "Sterile inflammation: sensing end reacting to damage", Nature Reviews Immunology, vol. 10, pp. 826-837, (2010).
Dinarello, C.A., "Anti-inflammatory Agents: Present and Future", Cell, vol. 140, Issue 6, pp. 935-950, (2010).
Ghosh, S., et al., "Hyaluronan fragments as mediators of inflammation in allergic pulmonary disease", Immunobiology, vol. 220, pp. 575-588, (2015).
Peri, F., et al., "Toll-like Receptor 4 (TLR4) Modulation by Synthetic and Natural Compounds: An Update", Journal of Medicinal Chemistry, vol. 57, pp. 3612-3622, (2014).
Ngkelo, A., et al., "New treatments for COPD", Current Opinion in Pharmacology, vol. 13, pp. 362-369, (2013).
Karbownik, M.S., et al., "Hyaluronan: Towards novel anti-cancer therapeutics", Pharmacological Reports, vol. 65, pp. 1056-1074, (2013).

* cited by examiner

*Primary Examiner* — Leigh C Maier

(74) *Attorney, Agent, or Firm* — Angela Lyon; Michael Fenwick

(57) ABSTRACT

The present disclosure relates to hyaluronic acid derivatives, and in particular, derivatives in which the N-acetyl group of hyaluronic acid has been substituted, and methods and uses thereof.

6 Claims, 22 Drawing Sheets

HYALURONIC ACID DERIVATIVES

RELATED APPLICATIONS

This application is a continuation of application Ser. No. 14/209,309, filed on Mar. 13, 2014, now U.S. Pat. No. 9,644,040, which claims the benefit of priority of U.S. provisional application No. 61/782,298 filed Mar. 14, 2013, the contents of which are incorporated herein by reference in their entirety

FIELD

The present disclosure relates to hyaluronic acid derivatives, and in particular, derivatives in which the N-acetyl group of hyaluronic acid has been substituted, and methods and uses thereof.

INTRODUCTION

Hyaluronan (hyaluronic acid) is a widely distributed glycosaminoglycan in animal tissues, composed of alternating monosaccharide units of N-acetyl glucosamine (N-acetyl-2-amido glucose) and glucuronic acid. Hyaluronan has multiple functions including hydration, provision of matrix for cell migration and lubrication of joints. Intact hyaluronan has a high molecular mass of greater than 1,000 kDa but can exist in lower molecular mass forms, for example, 100-250 kDa. Intact hyaluronan is often derived commercially from rooster comb or from bacterial sources. High molecular mass hyaluronans have high viscosity, which is important in lubricant properties of joints. However, the size and likely folding of the greater than 1,000 kDa hyaluronans presents a different physico-chemical milieu to cell receptors and the organization of interacting matrix macromolecules, than the smaller molecular mass forms. The high molecular mass hyaluronan is believed to be degraded enzymatically to lower mass fragments in tissues.

Innate immunity in humans is mediated through Toll-like receptors or TLR. A constitutively active TLR4 mutant can induce NF-kappa B activation and thus increase the production of pro-inflammatory cytokines (Medzhitov, R. et al. 1997, Nature 388:394). Recognition of bacterial lipopolysaccharide (LPS) by the innate immune system results in an inflammatory response characterized by the production of cytokines such as TNF, IL-1, IL-6, and IL-8; as well as gene activation of ICAM-1 (Lu Y. C. et al. Cytokine. 2008; 42:145-51). Hyaluronan can bind to a cell membrane receptor, CD44, and to a number of matrix proteins, notably the proteoglycan core protein link domain. CD44 has been reported to be up-regulated in some types of inflammatory arthritis, such as rheumatoid arthritis. Smaller molecular mass hyaluronans can interact with CD44 to activate cells that participate in inflammatory diseases and affect matrix molecules, which is generally not the case with high molecular mass hyaluronan (Horton M R. et al. J Biol Chem 1998 Vol. 273, No. 52, 35088-35094). A number of cytokines are induced and have higher levels in chronic inflammatory conditions. Humanized monoclonal antibodies to some of these cytokines are used therapeutically in chronic inflammatory conditions.

SUMMARY

The present disclosure relates to hyaluronic acid derivatives in which the N-acetyl group of hyaluronic acid has been removed or substituted with a different acyl functionality. Accordingly, in one embodiment, there is included a hyaluronic acid derivative comprising repeating units of a disaccharide unit comprising D-glucuronic acid and N-acetylglucosamine moieties, wherein a portion of the N-acetyl groups ($NHC(O)CH_3$) of the N-acetylglucosamine moiety of the disaccharide moieties are independently substituted with hydrogen or a group of the formula —N—C(O)—($C_2$-$C_{20}$)-alkyl, —N—C(O)—($C_2$-$C_{20}$)-alkenyl or —N—C(O)—($C_2$-$C_{20}$)-alkynyl, and wherein the hyaluronic acid derivative has a molecular weight of at least about 20 kDa, or a pharmaceutically acceptable salt, ester, or glucoside thereof.

In another embodiment, the hyaluronic acid derivative comprises repeating units of a disaccharide of the Formula (I) which has the structure

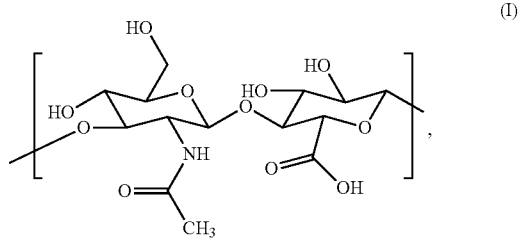

wherein a portion of the disaccharide units of the Formula (I) in the hyaluronic acid derivative are substituted (or replaced) with disaccharide units of the Formula (II)

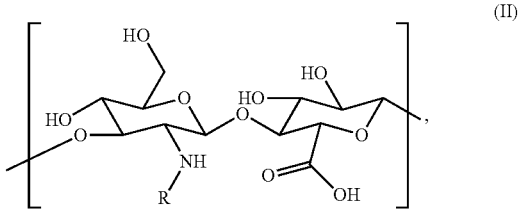

wherein R is H, —C(O)—($C_2$-$C_{20}$)-alkyl, —C(O)—($C_2$-$C_{20}$)-alkenyl or C(O)—($C_2$-$C_{20}$)-alkynyl.

In one embodiment, free hydroxyl groups, free carboxyl groups and/or free amino groups (when R is H) in the hyaluronic acid derivatives of the present disclosure, are reacted with a suitable cross-linker to form cross-linked hyaluronic acid derivatives, in which one or more hyaluronic acid derivatives of the present disclosure are cross-linked to form cross-linked polymers with varying degrees of gelation.

In another embodiment, when R is H, a portion of the disaccharide units of the Formula (II) are replaced with disaccharide units of the Formula (III), in which the free amine group (—$NH_2$) is reacted with a suitable cross-linker to form the structure of Formula (III)

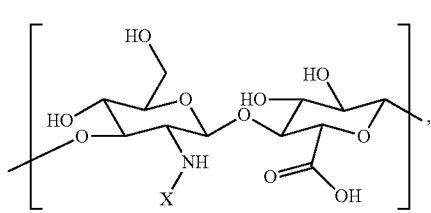

(III)

in which X is a suitable cross-linker.

In one embodiment, the cross-linker is biocompatible. In another embodiment, the cross-linker is (1R,4aS,5,7aS-tetrahydro-1-hydroxy-7-(hydroxymethyl)-cyclopenta[c]pyran-4-carboxylic acid, methyl ester (genipin)). Cross-linking reactions occur between, for example, the said free amines of the hyaluronic acid derivatives (when R is H) and the cross-linker (such as genipin) to yield cross-linked hyaluronic derivative polymers with various degrees of gelation. Such polymers may be admixed or further cross-linked with connective tissue components such as collagens and other matrix proteins and glycoproteins to form gels of different composition and biomechanical properties.

In one embodiment, the hyaluronic acid derivative comprises repeating units of a disaccharide which has the structure of the Formula (I)

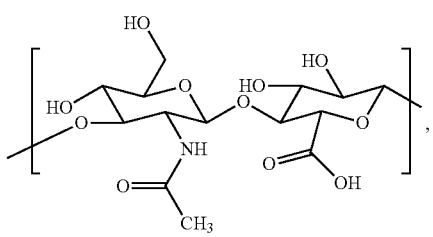

(I)

wherein a portion of the disaccharide units of the Formula (I) in the hyaluronic acid derivative are substituted with disaccharide units of the Formula (II)

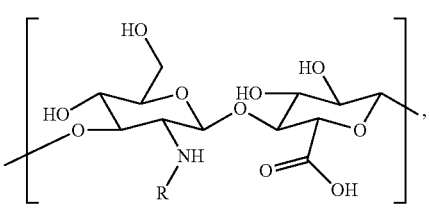

(II)

wherein R is H, —C(O)—($C_2$-$C_{20}$)-alkyl, —C(O)—($C_2$-$C_{20}$)-alkenyl or C(O)—($C_2$-$C_{20}$)-alkynyl,
and wherein a portion of the disaccharide units of the Formula (II) are substituted with disaccharide units of the Formula (III)

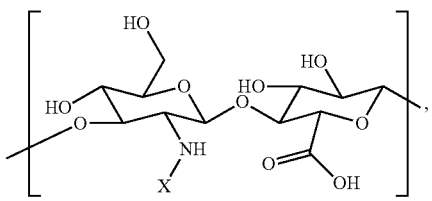

(III)

wherein X is any suitable cross-linker.

In one embodiment, the cross-linked hyaluronic acid derivative has the structure of the Formula (IV)

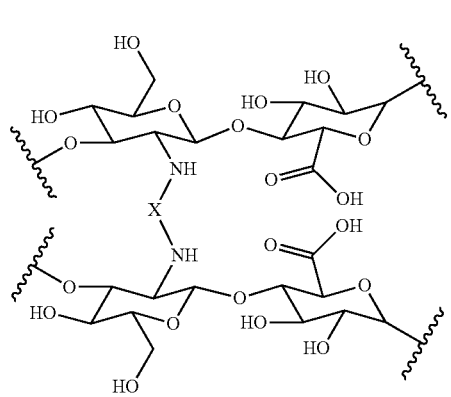

(IV)

wherein

indicates the repeating disaccharide units of the Formula (I), (II) and (III) of the hyaluronic acid derivatives of the present disclosure, wherein at least a portion, or all, of the units of the Formula (III) are cross-linked to another hyaluronic acid derivative to form cross-linked structures of the Formula (IV).

The hyaluronic acid derivatives and cross-linked derivatives of the present disclosure are useful for the treatment of conditions in which pro-inflammatory cytokines are involved. For example, the derivatives are useful for the treatment of inflammatory conditions degenerative rheumatic conditions, gastrointestinal inflammatory conditions, inflammatory diseases of the gums or periodontal structures, inflammatory diseases of the bladder, inflammatory diseases of the respiratory tract, inflammation associated with atherosclerosis, coronary heart disease or cerebrovascular disease or inflammatory conditions of the skin, including psoriasis, or diseases associated with a large release of cytokines such as septic shock.

In another embodiment, the cross-linked hyaluronic derivatives, either alone or mixed with other molecules of the connective tissue matrix such as collagen, are useful for the treatment of conditions where gelation or increased viscosity is an additional or restorative desirable property. Such conditions include, for example, repair of bone lesions or fractures, cartilage or other intra-articular lesions or injuries, conditions of ageing such as loss of substance of the skin for medical or cosmetic reasons, or conditions of the eye such as dry eyes, Sjogren's syndrome, or restoration of components of the vitreous in vitreous detachment, cataract formation or diseases or injuries of the cornea or supplementation to the manufacture or function of eye lenses. In one embodiment, the cross-linked hyaluronic derivatives may be also fashioned in sheets of required size and width for the purposes of covering burns and grafts in plastic and cosmetic surgery.

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

DRAWINGS

The disclosure will now be described in greater detail with reference to the following drawings in which.

DESCRIPTION OF VARIOUS EMBODIMENTS (I) Definitions

Figure 1:
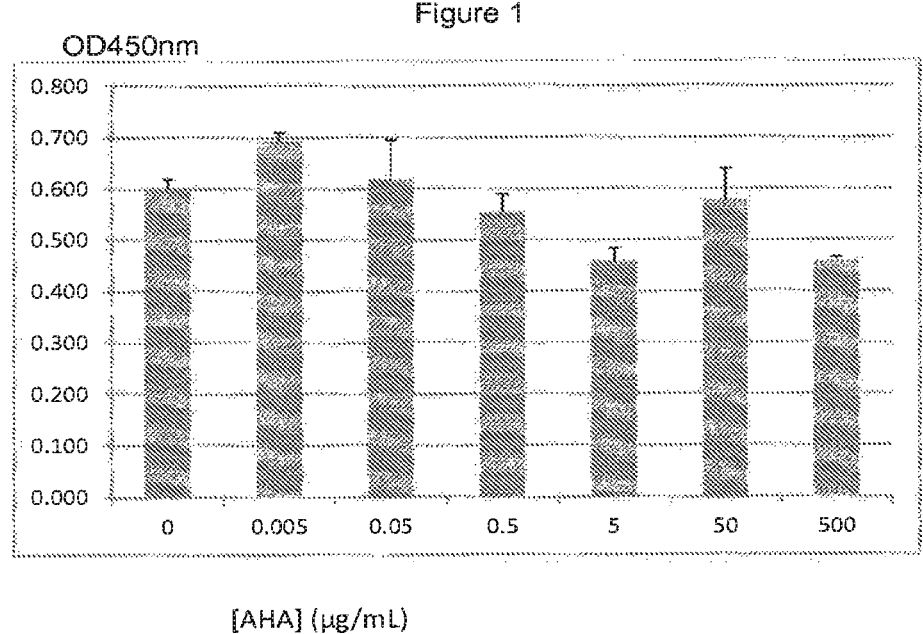
FIG. 1 is a bar graph showing the number of macrophage cultures with increasing concentrations of acetylated hyaluronic acid.

The term "hyaluronic acid" or "hyaluronan" is known in the art and as used herein refers to the glycosaminoglycan polymer composed of repeating units of the disaccharide comprised of glucoronic acid, for example D-glucoronic acid, and N-acetylglucosamine, for example, D-N-acetylglucosamine.

The term "derivative" as used herein refers to a substance which comprises the same basic carbon skeleton and functionality as the parent compound, but can also bear one or more substituents or substitutions of the parent compound. The term "derivative" includes those chemical modifications which involve the replacement of a portion of the N-acetyl groups of the N-acetylglucosamine of hyaluronic acid with a different acyl group or with a hydrogen. The term derivative also includes compounds in which a portion of the N-acetyl groups are reacetylated. Other derivatives include, for example, ester derivatives and include any compounds in which, in one embodiment, free hydroxyl groups of hyaluronic acid have been esterified (e.g. methyl esters, ethyl esters, benzyl esters etc.).

The term "cross-linked" as used herein means that two or more hyaluronic acid derivatives are covalently bonded inter-molecularly through a suitable cross-linking compound or agent or cross-linker. Alternatively, the cross-linking occurs intra-molecularly between sites of the same hyaluronic acid derivative. The cross-linking compound reacts with free hydroxyl groups, free carboxyl groups and/or free amino groups of the hyaluronic acid derivatives to form the cross-linked hyaluronic acid derivatives.

The term "cross-linker" or "cross-linking compound" or "cross-linking agent" as used herein refers to a compound which can react with at least two free hydroxyl groups, free carboxyl groups and/or free amino groups on a hyaluronic acid derivative as described in the present disclosure, and then react a second time to form a cross-linked hyaluronic acid derivative. The cross-linker can react intermolecularly to cross-link two or more different hyaluronic acid derivatives or intra-molecularly to cross-link two different positions of the same hyaluronic acid derivative.

The term "substituted" or "replaced" as used herein means that the N-acetyl group of the N-acetylglucosamine of hyaluronic acid is replaced with a selection from the indicated groups.

The term "a portion" as used herein refers to a part or fraction of the N-acetyl groups of the N-acetylglucosamine being substituted with a different acyl group or a hydrogen atom, or bonded to a cross-linker. For example, between 1 and 100% of the N-acetyl groups are replaced.

The term "N-acetyl group" as used herein is known in the art and refers the N-acetyl functionality of N-acetylglucosamine and has the chemical formula —N—C(O)—CH$_3$.

The term "alkyl" as used herein refers to straight or branched chain, saturated alkyl groups. The term ($C_2$-$C_n$)-alkyl means an alkyl group having at least two carbon atoms, and up to "n" carbon atoms, depending on the identity of "n". For example, ($C_2$-$C_{20}$)-alkyl includes alkyl groups having 2, 3, 4, 5, 6, 7, 8, 9, 10, 11, 12, 13, 14, 15, 16, 17, 18, 19 or 20 carbon atoms, and includes ethyl, propyl, isopropyl, butyl, sec-butyl, iso-butyl, etc.

The term "alkenyl" as used herein, whether it is used alone or as part of another group, means straight or branched chain, unsaturated alkenyl groups. The term $(C_2-C_n)$-alkenyl means an alkenyl group having at least two carbon atoms, and up to "n" carbon atoms, depending on the identity of "n". For example, $(C_2-C_{20})$-alkenyl includes alkenyl groups having 2, 3, 4, 5, 6, 7, 8, 9, 10, 11, 12, 13, 14, 15, 16, 17, 18, 19 or 20 carbon atoms, and includes ethenyl, propenyl, isopropenyl, butenyl, sec-butenyl, iso-butenyl, etc.

The term "alkynyl" as used herein, whether it is used alone or as part of another group, means straight or branched chain, unsaturated alkynyl groups. The term $(C_2-C_n)$-alkynyl means an alkynyl group having at least two carbon atoms, and up to "n" carbon atoms, depending on the identity of "n". For example, $(C_2-C_{20})$-alkynyl includes alkynyl groups having 2, 3, 4, 5, 6, 7, 8, 9, 10, 11, 12, 13, 14, 15, 16, 17, 18, 19 or 20 carbon atoms, and includes ethynyl, propynyl, isopropynyl, butynyl, sec-butynyl, iso-butynyl, etc.

The term "pharmaceutically acceptable salt" refers, for example, to a salt that retains the desired biological activity of a compound of the present disclosure and does not impart undesired toxicological effects thereto; and may refer to an acid addition salt or a base addition salt.

The term "acid addition salt" as used herein means any non-toxic organic or inorganic salt of any basic compound. Basic compounds that form an acid addition salt include, for example, compounds comprising an amine. For example, an acid addition salt includes any non-toxic organic or inorganic salt of any basic compound of the present disclosure. Inorganic acids that may form suitable salts include, without limitation, hydrochloric, hydrobromic, sulfuric and phosphoric acids, as well as metal salts such as sodium monohydrogen orthophosphate and potassium hydrogen sulfate. Organic acids that may form suitable salts include, without limitation, mono-, di-, or tricarboxylic acids such as glycolic, lactic, pyruvic, malonic, succinic, glutaric, fumaric, malic, tartaric, citric, ascorbic, maleic, benzoic, phenylacetic, cinnamic and salicylic acids, as well as sulfonic acids such as p-toluene sulfonic and methanesulfonic acids. Either the mono- or di-acid salts may be formed, and such salts may exist in either a hydrated, solvated or substantially anhydrous form. In general, acid addition salts are more soluble in water and various hydrophilic organic solvents, and generally demonstrate higher melting points in comparison to their free base forms. The selection of the appropriate salt will be known to a person skilled in the art.

The term "base addition salt" as used herein means any non-toxic organic or inorganic base addition salt of any acidic compound. Acidic compounds that form a base addition salt include, for example, compounds comprising a carboxylic acid group. For example, a base addition salt includes any non-toxic organic or inorganic base addition salt of any acidic compound of the present disclosure. Inorganic bases that may form suitable salts include, without limitation, lithium, sodium, potassium, calcium, magnesium or barium hydroxide. Organic bases that may form suitable salts include, without limitation, aliphatic, alicyclic or aromatic organic amines such as methylamine, trimethylamine and picoline or ammonia. The selection of the appropriate salt will be known to a person skilled in the art.

Those of ordinary skill in the art will recognize further pharmaceutically acceptable salts for the compounds provided herein. In general, a pharmaceutically acceptable acid addition salt or base addition salt is synthesized from a parent compound that contains a basic or acidic moiety by any conventional chemical method. For example, a neutral compound is treated with an acid or a base in a suitable solvent and the formed salt is isolated by filtration, extraction or any other suitable method.

In embodiments of the present disclosure, the compounds described herein have at least one asymmetric center. These compounds exist as enantiomers. Where compounds possess more than one asymmetric center, they may exist as diastereomers. It is to be understood that all such isomers and mixtures thereof in any proportion are encompassed within the scope of the present disclosure. It is to be further understood that while the stereochemistry of the compounds may be as shown in any given compound listed herein, such compounds may also contain certain amounts (e.g. less than 20%, suitably less than 10%, more suitably less than 5%) of compounds of the disclosure having alternate stereochemistry. For example, compounds of the disclosure that are shown without any stereochemical designations are understood to be racemic mixtures (i.e. contain an equal amount of each possible enantiomer or diastereomer). However, it is to be understood that all enantiomers and diastereomers are included within the scope of the present disclosure, including mixtures thereof in any proportion.

As used herein, the terms "treating" or "treatment" and the like refer to an approach for obtaining beneficial or desired results, including clinical results. Beneficial or desired clinical results may include, without limitation, alleviation or amelioration of one or more symptoms or conditions, diminishment of extent of disease, stabilization (i.e. not worsening) of the state of disease, prevention of development of disease, prevention of spread of disease, delay or slowing of disease progression, delay or slowing of disease onset or progression, amelioration or palliation of the disease state, diminishment of the reoccurrence of disease and remission (whether partial or total), whether detectable or undetectable. "Treating" or "treatment" may also refer to prolonging survival of a subject as compared to that expected in the absence of treatment. "Treating" or "treatment" may also refer to inhibiting the progression of disease, slowing the progression of disease temporarily or halting the progression of the disease permanently.

The term "administered" as used herein means administration of a therapeutically effective dose of a compound or composition of the disclosure to a subject.

The term "effective amount" or "therapeutically effective amount" as used herein means an amount effective, at dosages and for periods of time necessary to achieve the desired result. For example in the context of treating a subject with cancer, an effective amount is an amount that, for example, reduces the tumor volume compared to the tumor volume without administration of the compound of the present disclosure. Effective amounts may vary according to factors such as the disease state, age, sex and/or weight of the subject. The amount of a given compound that will correspond to such an amount will vary depending upon various factors, such as the given drug or compound, the pharmaceutical formulation, the route of administration, the type of condition, disease or disorder, the identity of the subject being treated, and the like, but can nevertheless be routinely determined by one skilled in the art.

As used herein, a "subject" refers to all members of the animal kingdom including mammals, and suitably refers to humans. A member of the animal kingdom includes, without limitation, a mammal (such as a human, primate, swine, sheep, cow, equine, horse, camel, canine, dog, feline, cat, tiger, leopard, civet, mink, stone marten, ferret, house pet, livestock, rabbit, mouse, rat, guinea pig or other rodent, seal, whale and the like), fish, amphibian, reptile, and bird (such as water fowl, migratory bird, quail, duck, goose, poultry, or chicken). In an embodiment of the present disclosure, the subject is in need of a compound or composition of the disclosure.

In understanding the scope of the present disclosure, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. The term "consisting" and its derivatives, as used herein, are intended to be closed terms that specify the presence of the stated features, elements, components, groups, integers, and/or steps, but exclude the presence of other unstated features, elements, components, groups, integers and/or steps. The term "consisting essentially of", as used herein, is intended to specify the presence of the stated features, elements, components, groups, integers, and/or steps as well as those that do not materially affect the basic and novel characteristic(s) of features, elements, components, groups, integers, and/or steps.

Terms of degree such as "about" and "approximately" as used herein mean a reasonable amount of deviation of the modified term such that the end result is not significantly changed. These terms of degree should be construed as including a deviation of at least ±5% or at least ±10% of the modified term if this deviation would not negate the meaning of the word it modifies.

(II) Hyaluronic Acid Derivatives of the Disclosure

The present disclosure relates to hyaluronic acid derivatives in which the N-acetyl group of hyaluronic acid has been removed or substituted with a different acyl functionality. Accordingly, in one embodiment, there is included a hyaluronic acid derivative comprising repeating units of a disaccharide unit comprising D-glucuronic acid and D-N-acetylglucosamine moieties, wherein a portion of the N-acetyl groups of the D-N-acetylglucosamine of the disaccharide unit have been substituted or replaced with hydrogen or a group of the formula —N—C(O)—($C_2$-$C_{20}$)-alkyl, —N—C(O)—($C_2$-$C_{20}$)-alkenyl or —N—C(O)—($C_2$-$C_{20}$)-alkynyl, and wherein the hyaluronic acid derivative has a molecular weight of at least about 20 kDa, or a pharmaceutically acceptable salt, ester, or glucoside thereof.

In one embodiment, the disaccharide repeating unit of the hyaluronic acid derivative has the structure of the Formula (I),

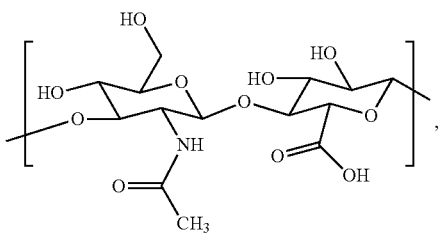

wherein a portion of the disaccharide units of the Formula (I) in the hyaluronic acid derivative are substituted or replaced with disaccharide units of the Formula (II),

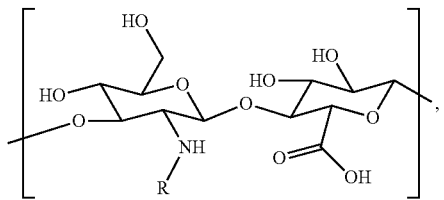

wherein R is H, —C(O)—($C_2$-$C_{20}$)-alkyl, —C(O)—($C_2$-$C_{20}$)-alkenyl or —C(O)—($C_2$-$C_{20}$)-alkynyl.

In one embodiment, R is H, —C(O)—($C_2$-$C_{16}$)-alkyl, —C(O)—($C_2$-$C_{16}$)-alkenyl or —C(O)—($C_2$-$C_{16}$)-alkynyl. In another embodiment, R is H, —C(O)—($C_2$-$C_{10}$)-alkyl, —C(O)—($C_2$-$C_{10}$)-alkenyl or —C(O)—($C_2$-$C_{10}$)-alkynyl. In a further embodiment, R is H, —C(O)—($C_2$-$C_6$)-alkyl, —C(O)—($C_2$-$C_6$)-alkenyl or —C(O)—($C_2$-$C_6$)-alkynyl. In an embodiment, R is H or —C(O)—($C_2$-$C_6$)-alkyl. The hyaluronic acid derivative according to claim 6, wherein R is H or —C(O)—($C_2$-$C_5$)-alkyl. In another embodiment, R is H, —C(O)-propyl, —C(O)-butyl, —C(O)-pentyl, —C(O)-isopentyl, or —C(O)-hexyl.

In other embodiments of the disclosure, the portion of N-acetyl groups (or portion of disaccharide units of Formula (I) replaced with units of Formula (II)) which are substituted is at least about 10%, or at least about 20%. In another embodiment, the portion of N-acetyl groups which are substituted is between about 10%-100%, or optionally between about 20% to about 80%. In other embodiments, the portion of N-acetyl groups which are substituted is at least about 1%, 2%, 5%, 10%, 20%, 30%, 40%, 50%, 60%, 70%, 80%, 90%, 95%, 98%, 99%, or 100%.

In another embodiment, the hyaluronic acid derivative of the present disclosure generally has a lower molecular weight when compared with the parent hyaluronic acid. Hyaluronic acid generally has a molecular weight of at least about 1,000 kDa. In one embodiment, the hyaluronic acid derivatives of the disclosure have a molecular weight of at least about 25 kDa, or at least about 30 kDa. In other embodiments, the derivative has a molecular weight of between about 20 kDa to about 500 kDa, or between about 20 kDa to about 250 kDa, or between about 50 kDa to about 250 kDa.

In another embodiment of the disclosure, the hyaluronic acid derivatives also include derivatives which have been re-acetylated. Accordingly, in one embodiment, there is included a hyaluronic acid derivative comprising repeating units of a disaccharide comprising D-glucuronic acid and D-N-acetylglucosamine, wherein a portion of the N-acetyl groups of the D-N-acetylglucosamine have been substituted with an N-acetyl functionality, and wherein the hyaluronic acid derivative has a molecular weight of at least about 20 kDa, or a pharmaceutically acceptable salt, ester, or glucoside thereof.

In one embodiment, free hydroxyl groups, free carboxyl groups and/or free amine groups (when R is H) in the hyaluronic acid derivatives of the present disclosure, are reacted with a suitable cross-linker to form cross-linked hyaluronic acid derivatives, in which one or more hyaluronic acid derivatives of the present disclosure are cross-linked to form cross-linked polymers having varying degrees of gelation.

In another embodiment, when R is H, a portion of the disaccharide units of the Formula (II), are replaced with disaccharide units of the Formula (III), in which the free amine group (—NH$_2$) are reacted with a suitable cross-linker to form the structure of Formula (III).

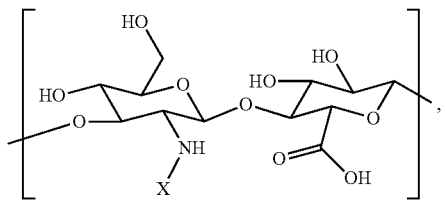

wherein X is any suitable cross-linker.

In one embodiment, the cross-linker is biocompatible. In another embodiment, the cross-linker is divinyl sulfone (DVS), 1-ethyl-3-(3-dimethylaminopropyl) (glutaraldehyde), 1-ethyl-3-(3-dimethylaminopropyl)carbodiimide (EDC), poly(ethyelene glycol) diglycidyl ether (EX 810), 3,3¢-dithiobis(propanoic dihydrazide) (DTPH), 1,3,5-benzene(tricarboxylic trihydrazide), or poly(ethylene glycol)-diamine tetrapropanoic tetrahydrazide. In another embodiment, the cross-linker is (1R,4aS,5,7aS-tetrahydro-1-hydroxy-7-(hydroxymethyl)-cyclopenta[c]pyran-4-carboxylic acid, methyl ester (genipin)). Cross-linking reactions occur between, for example, the said free amines of the hyaluronic acid derivative (when R is H) and the cross-linker (such as genipin) to yield hyaluronic derivative polymers with various degrees of gelation. Such polymers may be admixed or further cross-linked with connective tissue components such as collagens and other matrix proteins and glycoproteins to form gels of different composition and biomechanical properties.

In another embodiment, the hyaluronic acid derivatives of the present disclosure are cross-linked to biological, synthetic or biodegradable polymers, such as chitosan or collagen. In another embodiment, the hyaluronic acid derivatives of the present disclosure are cross-linked to glycoproteins, proteoglycans, proteins, peptides, or poly(2-hydroxyethylmethacrylate).

In one embodiment, the hyaluronic acid derivative comprises repeating units of a disaccharide which has the structure of the Formula (I)

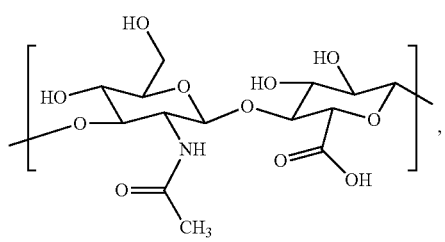

wherein a portion of the disaccharide units of the Formula (I) in the hyaluronic acid derivative are substituted or replaced with disaccharide units of the Formula (II)

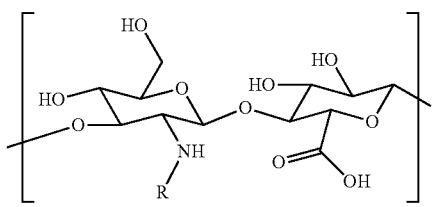

wherein R is H, —C(O)—(C$_2$-C$_{20}$)-alkyl, —C(O)—(C$_2$-C$_{20}$)-alkenyl or —C(O)—(C$_2$-C$_{20}$)-alkynyl, and wherein a portion of the disaccharide units of the Formula (II) are substituted or replaced with disaccharide units of the Formula (III)

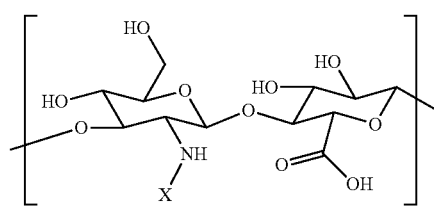

wherein X is any suitable cross-linker.

In one embodiment, the hyaluronic acid derivative comprises repeating units of a disaccharide which has the structure of the Formula (I)

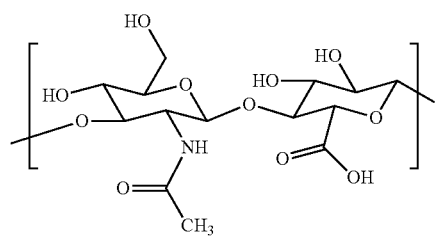

wherein a portion of the disaccharide units of the Formula (I) in the hyaluronic acid derivative are substituted or replaced with disaccharide units of the Formula (II)

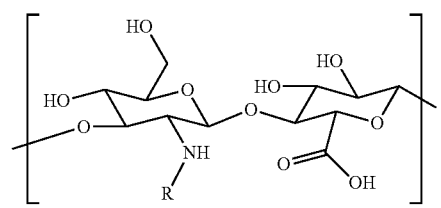

wherein R is H, —C(O)—(C$_2$-C$_{20}$)-alkyl, —C(O)—(C$_2$-C$_{20}$)-alkenyl or —C(O)—(C$_2$-C$_{20}$)-alkynyl, and wherein a portion of the disaccharide units of the Formula (II) are substituted or replaced with disaccharide units of the Formula (III)

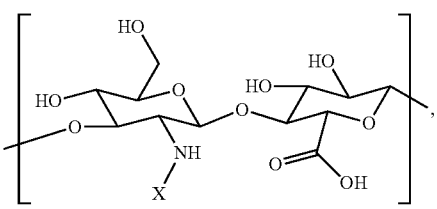

wherein X is any suitable cross-linker, in which the disaccharide units of the Formula (III) cross-link to form a structure of the Formula (IV)

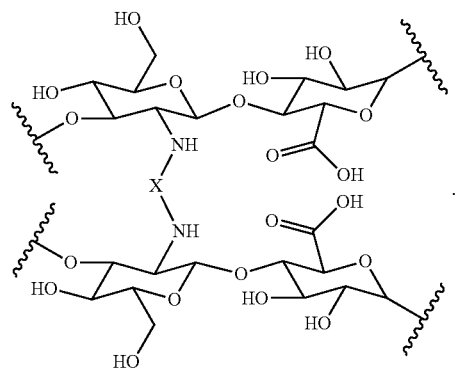

In one embodiment, the cross-linked hyaluronic acid derivative has the structure of the Formula (IV)

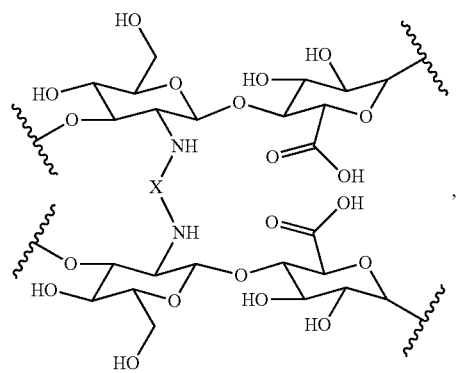

wherein

indicates the repeating disaccharide units of the Formula (I), (II) and (III) of the hyaluronic acid derivatives of the present disclosure, wherein at least a portion units of the Formula (III) are cross-linked to another hyaluronic acid derivative to form cross-linked structures of the Formula (IV).

In other embodiments of the disclosure, the hyaluronic acid derivatives are formulated as pharmaceutical compositions comprising a hyaluronic acid derivative as described herein and a pharmaceutically acceptable excipient or carrier. In various embodiments, the pharmaceutical composition comprises one or more compounds of the present disclosure and one or more nontoxic, pharmaceutically acceptable carriers and/or diluents and/or adjuvants and/or excipients, and optionally a therapeutic agent.

The hyaluronic acid derivatives of the present disclosure are compatible with mixing in a suitable vehicle in which the derivative is either dissolved or suspended. The derivatives may be dissolved in water, salt solutions, other pharmaceutically acceptable solvents, either alone or in combination with compatible nutrients, antibiotics, or combined with other medications.

In one embodiment, the hyaluronic acid derivatives of the disclosure can be admixed with a preparation of the parent hyaluronan (hyaluronic acid) in a solution or suspension and will be compatible with mixing in a suitable vehicle in which the active ingredient is either dissolved or suspended. The parent hyaluronan may be derived from a mammalian or bacterial source or may be synthetic.

The hyaluronic acid derivatives of the disclosure can be administered to an animal in an effective, therapeutic amount, by various routes of administration, including but not limited to: orally, subcutaneously, intramuscularly, intravenously, trans-dermally, intra-articularly, rectally, by colonic enema, in a mouth wash, in a gingival ointment, or by bladder instillation. The hyaluronic acid derivatives of the disclosure may be mixed with food or feed or may be administered in a suitable vehicle, in which the active ingredient is either dissolved or suspended. Solution compositions may be water, salt solutions, and other solvents either alone or in combination with compatible nutrients, antibiotics, drugs suited to the condition, including the medical condition of the mammal.

A hyaluronic acid derivative of the present disclosure may be orally administered, for example, with an inert diluent or with an assimilable edible carrier, or it may be enclosed in hard or soft shell gelatin capsules, or It may be compressed into tablets, or it may be incorporated directly with the food of the diet. For oral therapeutic administration, the derivative may be incorporated with excipient and used in the form of ingestible tablets, buccal tablets, troches, capsules, elixirs, suspensions, syrups, wafers, and the like. Oral dosage forms also include modified release, for example immediate release and timed-release, formulations. Examples of modified-release formulations include, for example, sustained-release (SR), extended-release (ER, XR, or XL), time-release or timed-release, controlled-release (CR), or continuous-release (CR or Contin), employed, for example, in the form of a coated tablet.

A hyaluronic acid derivative of the present disclosure may also be administered parenterally. Solutions of a derivative of the present disclosure can be prepared in water suitably mixed with a surfactant such as hydroxypropylcellulose. Dispersions can also be prepared in glycerol, liquid polyethylene glycols, DMSO and mixtures thereof with or without alcohol, and in oils. Under ordinary conditions of storage and use, these preparations contain a preservative to prevent the growth of microorganisms. A person skilled in the art would know how to prepare suitable formulations.

The hyaluronic acid derivatives of the disclosure may be admixed with naturally occurring hyaluronan (hyaluronic acid) of any molecular weight and viscosity, of mammalian or bacterial origin, for the purpose of administering to a mammal by any of the said routes above as a method of treatment for a chronic or acute inflammatory condition or a degenerative condition in a mammal.

Kits and commercial packages for use in the therapeutic, diagnostic and research applications described herein are also within the scope of the present disclosure. In one embodiment, a kit or commercial package may comprise a hyaluronic acid derivative of the present disclosure or a composition comprising a derivative of the present disclosure together with instructions for using the kit. Further, the kit may comprise one or more reagents, buffers, packaging materials, and containers for holding the components of the kit.

(III) Processes for Preparing Derivatives

In embodiments of the disclosure, the hyaluronic acid derivatives are prepared from hyaluronic acid by removal of the N-acetyl group, —C(O)CH$_3$, resulting in deacetylated hyaluronic acid having a free amino group, —NH$_2$, as a derivative of the disclosure. In one embodiment, the acetyl group is removed using a hydrazinolysis reaction, by reacting, for example, hyaluronic acid with hydrazine or a hydrazine containing reactant.

Other acyl-substituted derivatives of the present disclosure can be prepared from the deacetylated hyaluronic acid by addition of an acyl group, for example, by using an acyl-donating reactant. Examples of acyl-donating reactants include acyl-anhydride or acyl chlorides, such as for example, butyryl anhydride, butyryl chloride etc. Acyl substituted hyaluronic acid derivatives of the present disclosure are isolated from the reaction of the deacetylated hyaluronic acid and the acyl-donating group.

In certain embodiments, the portion of N-acetyl groups which are removed and subsequently replaced with other acyl groups or hydrogen is dependent on the amount of hydrazine (or a hydrazine containing reactant) which is used in the deacetylation reaction and the length of time the reaction is allowed to proceed. Higher concentrations of hydrazine (or a hydrazine containing reactant) and/or longer reaction times, will increase the portion of acetyl groups which are removed from the hyaluronic acid, and subsequently increase the yield of the hyaluronic acid derivatives of the present disclosure. In further embodiments, the portion of acetyl groups which are replaced with other acyl groups or hydrogen (or reacetylated) is also dependent upon the amount of acyl donating group which is used in the reaction to form the acyl-substituted derivatives, as well as the length of time the reaction is allowed to proceed. Higher concentrations of the acyl donating reactant and/or longer reaction times, will increase the portion of acyl-substituted groups in the hyaluronic acid derivatives.

In another embodiment, cross-linked hyaluronic acid derivatives are prepared by adding a cross-linker to the hyaluronic acid derivatives of the present disclosure. In one embodiment, the degree of gelation of the cross-linked hyaluronic acid derivatives (or polymers) is controlled by adjusting the concentrations of the hyaluronic acid derivatives and/or the cross-linker, or by selection of the cross-linker. In one embodiment, the cross-linker is genipin.

In another embodiment, the cross-linking is achieved by polymerizing the cross-linking agent, such as genipin, in the presence of the hyaluronic acid derivatives, such that the cross-linking agent is an oligomer or macromer. In another embodiment, the cross-linking reaction is conducted in the presence of connective tissue components such as collagens, other matrix proteins and glycoproteins.

(IV) Methods of Treatment

The hyaluronic acid derivatives of the present disclosure are useful for diseases or conditions in which the modulation or inhibition of the production of inflammatory cytokines is beneficial. A person skilled in the art would understand that increased cytokine production plays an important role in diseases or conditions in which inflammation plays a role. The derivatives of the present disclosure are able to modulate or inhibit the production of inflammatory cytokines, which occurs as a result of stimulation by, for example, lower molecular mass hyaluronan, lipopolysaccharlde or other microbial stimulants.

In macrophage cell culture tests, the hyaluronic acid derivatives of the present disclosure have been found to be non-toxic to the cells, and generally do not elicit an immune response.

In one embodiment of the disclosure there is included a method for the treatment of inflammation comprising administering to a patient in need thereof a hyaluronic acid derivative or composition as described herein. In another embodiment, there is included a use of a hyaluronic acid derivative or composition as described herein for the treatment of inflammation. In one embodiment, the inflammation results from the production of pro-inflammatory cytokines in the patient. In one embodiment, the pro-inflammatory cytokines are selected from IL1-β, IL6, IL8, MCP1, and TNF-α.

In another embodiment, there is included a method for the treatment of an inflammatory condition or degenerative rheumatic condition comprising administering to a patient in need thereof a hyaluronic acid derivative or composition as described herein. In another embodiment, there is included a use of a hyaluronic acid derivative or composition as described herein for the treatment of an inflammatory condition or degenerative rheumatic condition. The rheumatic condition, for example, is rheumatoid arthritis, psoriatic arthritis, chronic tophaceous gout, acute gout, ankylosing spondylitis, connective tissue diseases, vasculitis, or osteoarthritis.

Also included in the disclosure is a method for the treatment of a gastrointestinal inflammatory condition comprising administering to a patient in need thereof a hyaluronic acid derivative or composition as described herein. In another embodiment, there is included a use of a hyaluronic acid derivative or composition as described herein for the treatment of a gastrointestinal inflammatory condition. The gastrointestinal inflammatory condition, for example, is inflammatory bowel disease, Crohn's disease, or ulcerative colitis.

The present disclosure includes a method for the treatment of an inflammatory disease of the gums or periodontal structures comprising administering to a patient in need thereof a hyaluronic acid derivative or composition as described herein. In another embodiment, there is included a use of a hyaluronic acid derivative or composition as described herein for the treatment of an inflammatory disease of the gums or periodontal structures. The disease associated with the gums or periodontal structures is, for example, gingivitis or inflammatory periodontal disease.

In another embodiment, the present disclosure also includes a method for the treatment of an inflammatory disease of the bladder comprising administering to a patient in need thereof a hyaluronic acid or composition as described herein. In another embodiment, there is included a use of a hyaluronic acid derivative or composition as described herein for the treatment of an inflammatory disease of the bladder. The inflammatory disease of the bladder, for example, is acute interstitial cystitis or chronic interstitial cystitis.

In a further embodiment, there is included a method for the treatment of an inflammatory disease of the respiratory tract comprising administering to a patient in need thereof a hyaluronic acid derivative or composition as described herein. In another embodiment, there is included a use of a hyaluronic acid derivative or composition as described herein for the treatment of an inflammatory disease of the respiratory tract. The inflammatory disease of the respiratory tract is, for example, acute asthma, chronic asthma, chronic obstructive lung disease, interstitial lung disease, or Bronchiolitis obliterans organizing pneumonia.

The hyaluronic acid derivatives and cross-linked derivatives of the present disclosure are useful for the treatment of conditions in which pro-inflammatory cytokines are involved. For example, the derivatives are useful for the treatment of inflammatory conditions degenerative rheumatic conditions, gastrointestinal inflammatory conditions, inflammatory diseases of the gums or periodontal structures, inflammatory diseases of the bladder, inflammatory diseases of the respiratory tract, inflammation associated with atherosclerosis, coronary heart disease or cerebrovascular disease or inflammatory conditions of the skin, including psoriasis, or diseases associated with a large release of cytokines such as septic shock.

In another embodiment, the cross-linked hyaluronic derivatives, either alone or mixed with other molecules of the connective tissue matrix such as collagen, are useful for the treatment of conditions where gelation or increased viscosity is an additional or restorative desirable property. Such conditions include, for example, repair of bone lesions or fractures, cartilage or other intra-articular lesions or injuries, conditions of ageing such as loss of substance of the skin for medical or cosmetic reasons, or conditions of the eye such as dry eyes, Sjogren's syndrome, or restoration of components of the vitreous in vitreous detachment, cataract formation or diseases or injuries of the cornea or supplementation to the manufacture or function of eye lenses. In one embodiment, the cross-linked hyaluronic derivatives may be also fashioned in sheets of required size and width for the purposes of covering burns and grafts in plastic and cosmetic surgery.

In another embodiment, the disclosure includes a method for the treatment of a disease associated with the release of cytokines comprising administering to a patient in need thereof a hyaluronic acid derivative or composition as described herein, wherein the cytokines have the potential to cause damage to organs in a mammal. In one embodiment, the disease associated with the release of cytokines is a bacterial infection, such as septic shock.

In another embodiment of the disclosure, the cross-linked hyaluronic acid derivatives are injected, or introduced by surgical procedures, including arthroscopic, endoscopic procedures and computer guided imaging, into soft tissue or hard tissue, such as cartilage or bone. Such surgical procedures include those used in cosmetic and reconstructive surgery.

In another embodiment, the cross-linked hyaluronic acid derivatives (gels) are prepared as sheets to be used in applications where large surface areas are covered. For example, the gels are prepared as sheets having a desirable size and consistency, wherein the sheets are used to treat burns or are used in skin graft operations. In another embodiment, the crosslinked hyaluronic acid derivatives are used as artificial matrices to grow cells, such as skin fibroblasts or other skin cells, so as to produce artificial skin to be used in burns or skin graft operations.

In another embodiment, the cross-linked hyaluronic acid derivatives can be cross-linked or other-wise incorporated into artificial polymers suitable for optical lenses and utilized in the production of said optical lenses.

EXAMPLES

The following non-limiting examples are illustrative of the present disclosure:

Materials and Methods:

Hyaluronic acid sodium salt from *Streptococcus equi* (HA), Hydrazine monohydrate, Hydrazine sulphate salt, iodomethane, iodic acid, Acetic anhydride and Butyric anhydride were all obtained from Sigma Aldrich®. Ethanol and Acetone was obtained from Fishers®. The Human IL-1B ELISA kit (pre-coated) was obtained from Cedarlane®. RPMI-1640 media was obtained from ATCC®. AGAROSE (Biotechnology grade) was obtained from BioShop®. Electrophoresis gel running system (mini-horizontal unit) was obtained from Fisher)@ scientific. Power pack for running the gel was obtained from E-C apparatus Corporation®, Model no FB-EC600-90. Human acute monocytic leukemia (THP-1 cells) was obtained from ATCC®. Liposaccharide (LPS) and Triza base were obtained from Sigma Aldrich®. Boric acid was obtained from Fishers®. All stains (95%) was obtained from sigma Aldrich.

Example 1: Synthesis, Characterization and Analysis of N-Acylated Hyaluronans (a) Partial Deacetylation of Hylauronic Acid To 6 g of hyaluronic acid was added 300 mL of hydrazine monohydrate (2% w/V polymer solution). To this solution, was added 3 g of hydrazine sulfate, and the resulting solution stirred for 72-96 hours at 55° C. After this time, 120 mL of cold ethanol was added to precipitate the hyaluronic polymeric product. The precipitated product was then collected and washed with ethanol, and dried under vacuum for 24 hours.

To 100 mL of acetic acid (5%) was added 60 mL of 0.5M iodic acid ($HIO_3$). To this solution was added the precipitate and the solution stirred in a bath at 4° C. for at least 1 hour. After stirring, 17.5 mL of aqueous HI ($CH_3I$) was added and the mixture stirred for 15 minutes.

The violet solution was then transferred to a separatory funnel to which was added 150 mL of diethyl ether. The mixture was vigorously stirred for a few minutes and the aqueous layer recovered. The separation was repeated with diethyl ether until the violet colour has dissipated from the organic layer. The pH aqueous solution was then adjusted to 7-7.5 with 0.2 M NaOH. Ethanol was then added to the solution to precipitate the polymer, which was then dialyzed against double distilled water and freeze dried resulting in the deacetylated hyaluronan. The freeze dried sample was then analyzed using $^1$HNMR, $^{13}$CNMR, H—H COSY and H—H TOSCY.

(b) N-Acylation of Partial Deacetylated of Hylauronic Acid 0.1 g of the product from part (a) was dissolved in 30 mL of water, to which was added 6 mL of saturated $NaHCO_3$ and 6 mL of 5% v/v butyric anhydride in absolute alcohol. The solution was intermittently stirred for 5-10 minutes until the smell of acyl anhydride was reduced. The reaction was quenched by putting in a 100° C. bath for 3-5 minutes and then cooled to room temperature. The solution was then tested with an Ehrlich assay. The solution was then purified on amberlite and the supernatant freeze dried to obtain the product. The freeze dried sample was then analyzed using $^1$HNMR, $^{13}$CNMR, H—H COSY and H—H TOSCY.

Example 2: Analysis of N-Acylated Hyaluronans on Agarose Gels

Designations:
(i) HA, native, parent hyaluronan high molecular weight, bacterial origin (hyaluronic acid); (ii) AHA, (re)-N-acetylated hyaluronan; (iii) BHA, N-butyrylated hyaluronan; (iv) DHA, de-acetylated hyaluronan.

10 mg/ml of the polymer solution was prepared in distilled water (HAo, AHAo, BHAo and DHAo). 500 uL of the solution was centrifuged at 14,000 g for 10 minutes using a NANOSEP™ microconcentrator with a molecular weight cut off of 300 KDa (HA1, AHA1, BHA1 and DHA1). 200 uL of the filtrate from above was centrifuged at 14,000 g for 10 minutes using a NANOSEP™ microconcentrator with a molecular weight cut off of 100 KDa (HA2, AHA2, BHA2 and DHA2). Any residual that did not pass through the 300 kDa NANOSEP™ microconcentrator was dissolved in 500 uL of water (HA3, AHA3, BHA3 and DHA3). 20 ul of the solution was mixed with 4 ul of loading dye. 20 uL of the resulting solution was loaded on a 1% agarose gel and was run for 1 hour at 100V. The gels were stained overnight in 0.005% stains all dissolved in 50% (v/v) ethanol.

The molecular weight of the hyaluronic acid from Sigma (HA), the deacetylated HA (DHA), the reacetylated HA (AHA) and butyrylated HA (BHA) obtained using the agarose gel is semi quantitative and the estimated molecular weight range of the samples are shown in Table 1.

Example 3: Effect of Synthetic N-Acyl Hyaluronans on Cell Culture Model of Inflammation The monocyte/macrophage THP-1 cell line was purchased from Cedarlane, Canadian distributor for ATCC. The cat # is ATCC TIB-202.

The cell line was maintained in suspension culture (=monocytes) in RPMI-1640 (Cedarlane cat #30-2001). This medium was supplemented with 50 µM ß-mercaptoethanol, 100 nm PMA and 10% FBS. The culture was seeded at 2 to $4 \times 10^5$ cells/mL and subcultured when the cell density reached 8 to $10 \times 10^5$. The cell density was not allowed to exceed $10 \times 10^5$ cells/mL. The new subcultures were then setup by diluting at the required cells/mL with fresh medium and not by centrifugation with the additions of the synthetic hyaluronans (500 µg/ml) or LPS (1 µg/ml). After 24 hours, the medium was collected for the cytokine ELISAs, as indicated below. The cells were counted using the XTT/PMS cell proliferation assay utilizing a commercial assay kit.

Cytokine Formation in Presence of DHA, AHA and BHA in the Presence or Absence of LPS As shown in FIG. 1, by the assay for cell numbers, there is no change in cell numbers suggesting no cell toxicity was observed with increasing concentrations of AHA, ((re)-N-acetylated hyaluronan).

Figure 2:
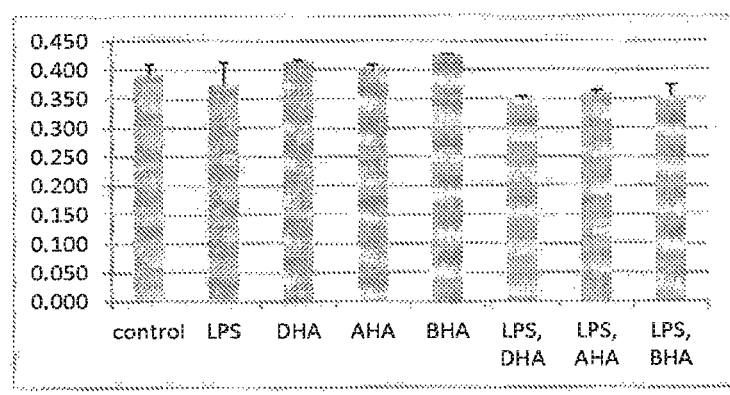
FIG. 2 is a bar graph showing the number of macrophage cultures with addition of compounds of the disclosure.

As shown in FIG. 2, no cell toxicity was observed with the addition of DHA, AHA or BHA, alone or in combination with LPS, as the tryptan blue exclusion viability tests were negative. The compounds were also shown to be stable after 3 months at −20° C.

Figure 3:
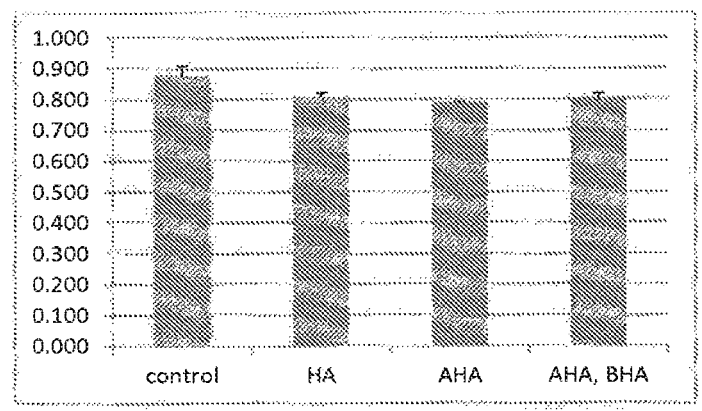
FIG. 3 is a bar graph showing the number of macrophage cultures with addition of compounds of the disclosure.

As shown in FIG. 3, no cell toxicity was observed with the addition of HA, AHA, or a combination of AHA and BHA.

Figure 4:
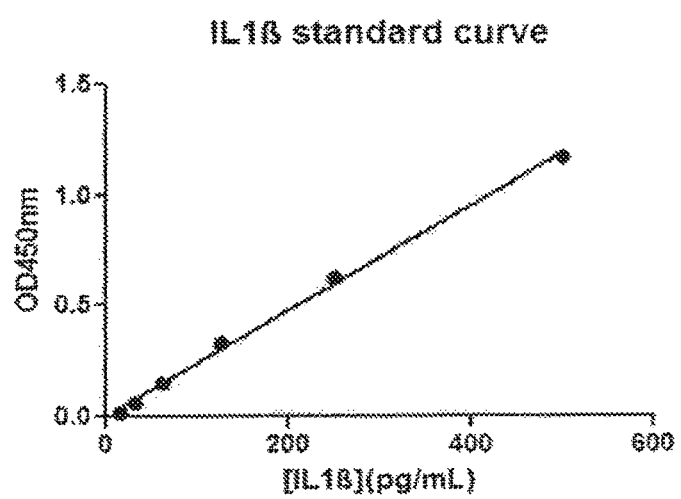
FIG. 4 is a graph showing the standard curve for IL-1-β.

FIG. 4 shows a standard ELISA calibration curve for IL1β, at 450 nm.

Figure 5:
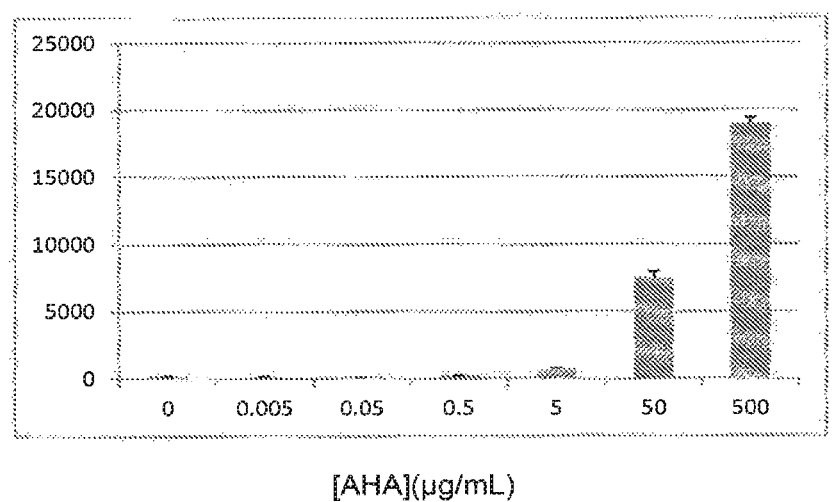
FIG. 5 is a bar graph showing a dose response for IL-1-β formation with concentration of acetylated hyaluronic acid.

FIG. 5 shows a dose response bar graph on the formation of IL1β, and demonstrates that increasing concentrations of AHA result in increased production of IL1β. As AHA is a re-acetylated, relatively small molecular mass hyaluronan prepared from de-acetylated hyaluronan, AHA is considered to be equivalent to naturally occurring hyaluronans of similar molecular mass.

Figure 6:
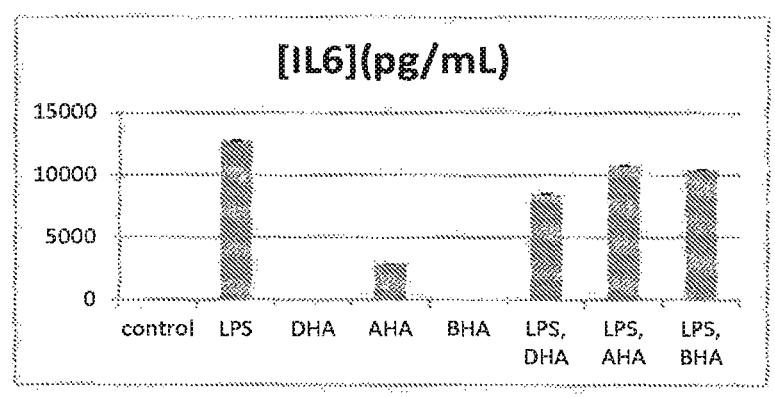
FIG. 6 is a bar graph showing the effect of compounds of the disclosure on IL-6 synthesis.

FIG. 6 shows a bar graph on the effect of various compounds of the disclosure on the formation of IL6. Addition of DHA and BHA results in almost no stimulation of IL6 synthesis, while the addition of AHA results in modest synthesis of IL6. LPS was used as a positive control showing a maximal level of stimulation. The addition of DHA, AHA or BHA with LPS results in a modest reduction of the LPS stimulation on IL6 synthesis.

Figure 7:
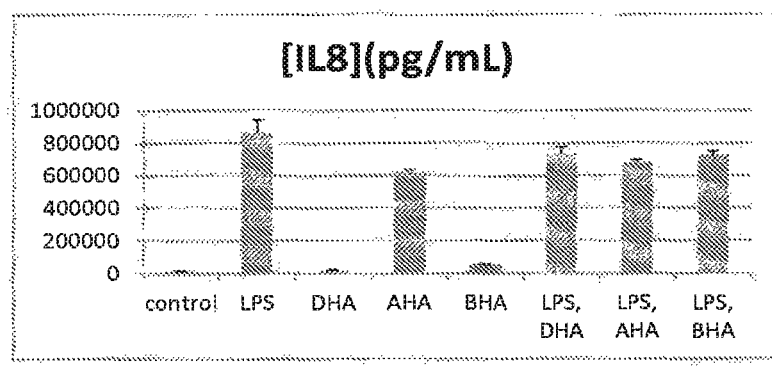
FIG. 7 is a bar graph showing the effect of compounds of the disclosure on IL-8 synthesis.

FIG. 7 shows a bar graph on the effect of various compounds of the disclosure on the formation of IL8. Addition of DHA and BHA results in very low levels of IL8 synthesis, while the addition of AHA results in rather high levels of IL8 synthesis. LPS was used as a positive control showing a maximal level of stimulation. The addition of DHA, AHA or BHA with LPS results in a modest reduction of the LPS stimulation on IL8 synthesis.

Figure 8:
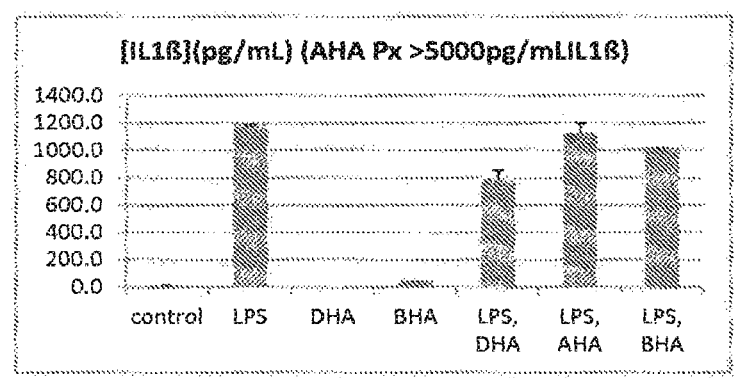
FIG. 8 is a bar graph showing the effect of compounds of the disclosure on IL-8β synthesis.

FIG. 8 shows a bar graph on the effect of various compounds of the disclosure on the formation of IL1β. Addition of DHA and BHA results in almost no stimulation of the levels of IL1β synthesis, while the addition of AHA also resulted in no stimulation (not shown). LPS was used as a positive control showing a maximal level of stimulation. The addition of DHA or BHA with LPS results in a modest reduction of the LPS stimulation on IL1β synthesis, while addition of AHA had no significant effect.

Figure 9:
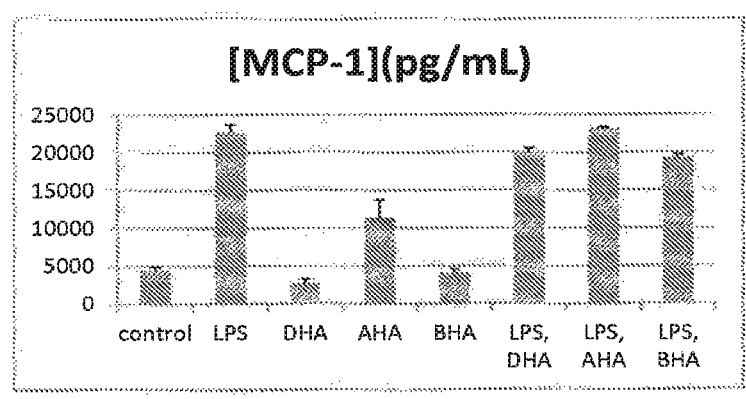
FIG. 9 is a bar graph showing the effect of compounds of the disclosure on formation of MCP-1.

FIG. 9 shows a bar graph on the effect of various compounds of the disclosure on the formation of MCP-1. Addition of DHA and BHA results in low levels of MCP-1 synthesis, while the addition of AHA results in rather moderate levels of stimulation. LPS was used as a positive control showing a maximal level of stimulation. The addition of DHA or BHA with LPS results in a modest reduction of the LPS stimulation on MCP-1 synthesis, while addition of AHA had no significant effect.

Figure 10:
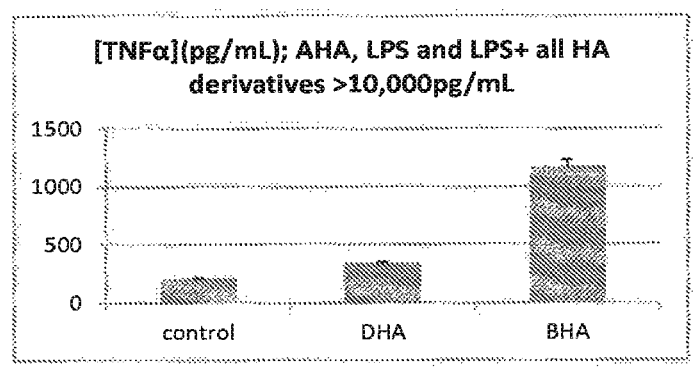
FIG. 10 is a bar graph showing the effect of compounds of the disclosure on formation of TNF-α.

FIG. 10 shows a bar graph on the effect of various compounds of the disclosure on the formation of TNF-α. Addition of DHA and BHA results in very low levels of stimulation on TNF-α synthesis. The addition of AHA, LPS and LPS with any other compound resulted in high levels of synthesis (over 1000-fold). LPS was used as a positive control showing a maximal level of stimulation. The addition of DHA or BHA with LPS results in a modest reduction of the LPS stimulation on IL1β synthesis, while addition of AHA had no significant effect.

Cytokine Formation in Presence of HA, AHA, and AHA and BHA

Figure 11:
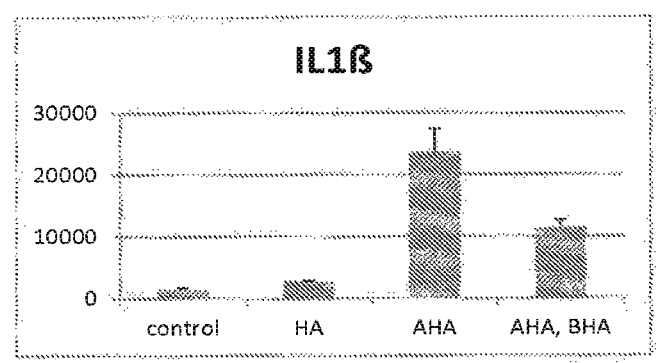
FIG. 11 is a bar graph showing the effect of compounds of the disclosure on formation of IL-1β synthesis.

FIG. 11 shows a bar graph on the effect of HA, AHA and AHA+BHA on the synthesis of IL1β. The addition of HA had a very small effect on IL formation compared to the control, while the addition of AHA caused a large effect on IL1β formation. The addition of AHA and BHA resulted in a decline of the stimulation of IL1β caused by the addition of AHA alone.

Figure 12:
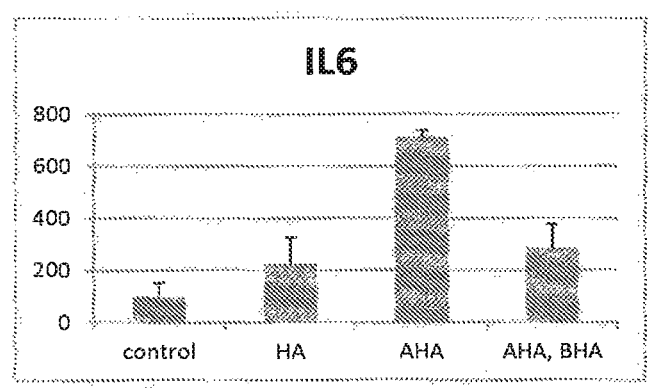
FIG. 12 is a bar graph showing the effect of compounds of the disclosure on formation of IL-6.

FIG. 12 shows a bar graph on the effect of HA, AHA and AHA+BHA on the synthesis of IL6. The addition of HA had a very small effect on IL6 formation compared to the control, while the addition of AHA caused a large effect on IL6 formation. The addition of AHA and BHA resulted in a decline of the stimulation of IL6 caused by the addition of AHA alone.

Figure 13:
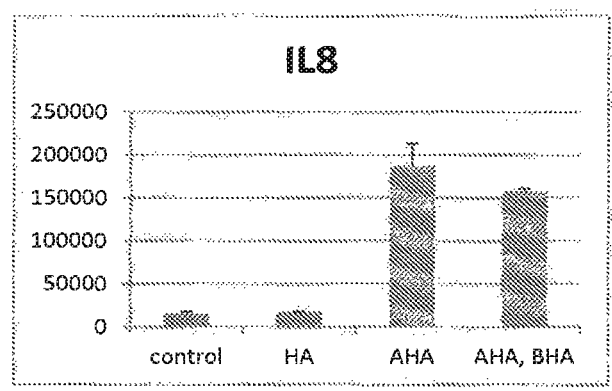
FIG. 13 is a bar graph showing the effect of compounds of the disclosure on formation of IL-8.

FIG. 13 shows a bar graph on the effect of HA, AHA and AHA+BHA on the synthesis of IL8. The addition of HA had a very small effect on IL8 formation compared to the control, while the addition of AHA caused a large effect on IL8 formation. The addition of AHA and BHA resulted in a decline of the stimulation of IL18 caused by the addition of AHA alone.

Figure 14:
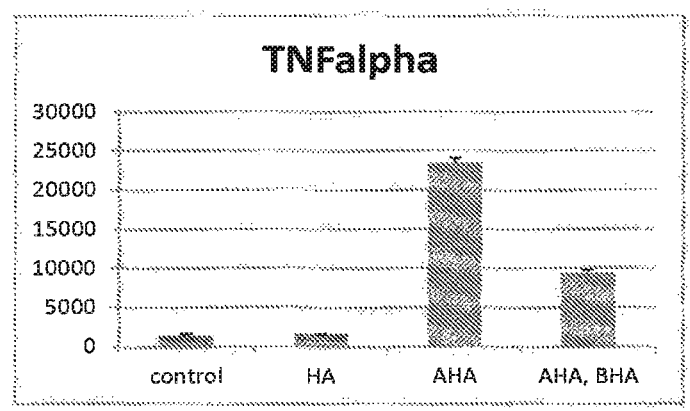
FIG. 14 is a bar graph showing the effect of compounds of the disclosure on formation of TNF-α.

FIG. 14 shows a bar graph on the effect of HA, AHA and AHA+BHA on the synthesis of TNF-α. The addition of HA had a very small effect on TNF-α formation compared to the control, while the addition of AHA caused a large effect on TNF-α formation. The addition of AHA and BHA resulted in a decline of the stimulation of TNF-α caused by the addition of AHA alone.

Example 4: Analysis of N-Acylated Hyaluronans on Agarose Gels

Figure 15:
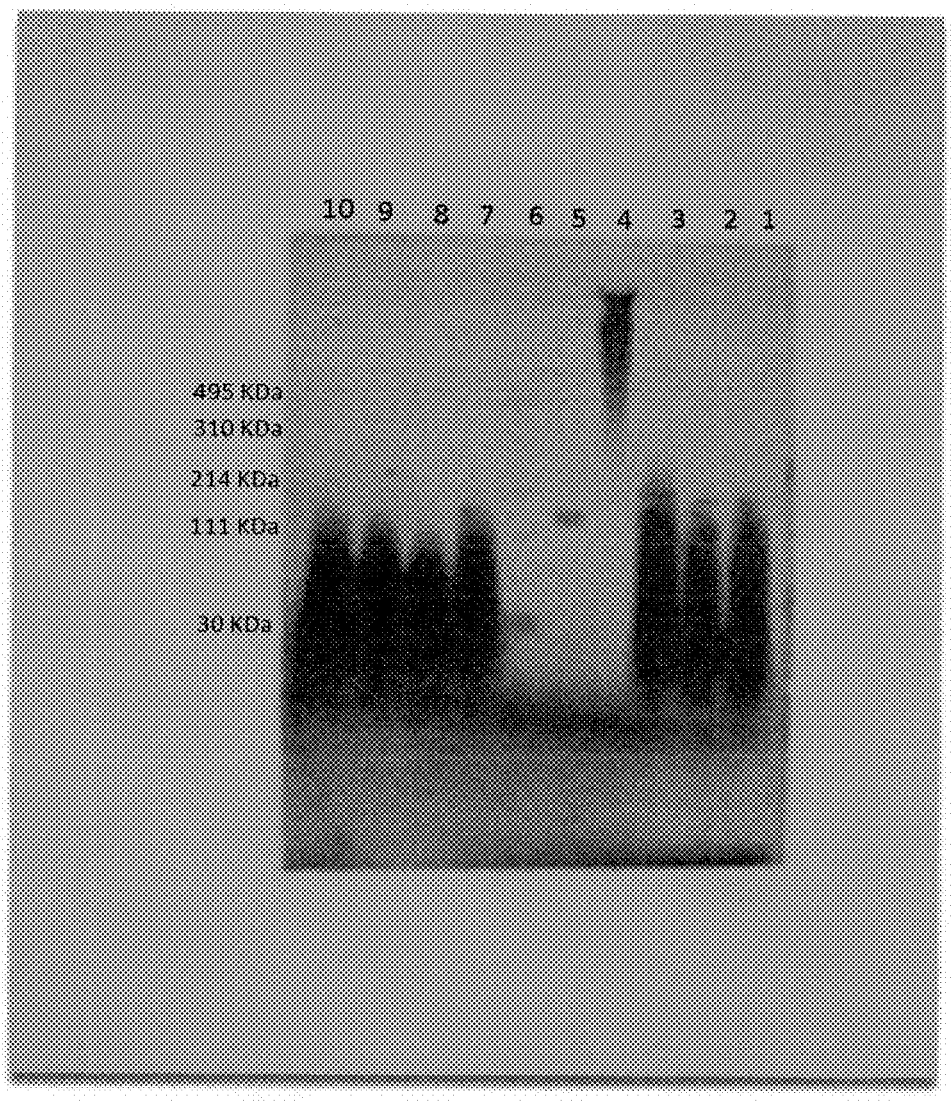
FIG. 15 shows an agarose gel of various hyaluronic acid derivatives.

Various hyaluronic acid derivatives were synthesized according to the method of Example 1 and analyzed on agarose gel according to Example 2. As shown in FIG. 15, the following derivatives were synthesized:
Lane 1 is AHAo
Lane 2 is BHAo
Lane 3 is DHAo
Lane 4 is HAo
Lane 5 is the standard with molecular weight of 125-175 KDa
Lane 6 is the HA ladder standard
Lane 7 is HHAo (hexanoyl substituted HA)
Lane 8 is IVHAo (isovaleryl substituted HA)
Lane 9 is PHAo (propionyl substituted HA)
Lane 10 is VHAo (valeryl substituted HA)

Figure 16:
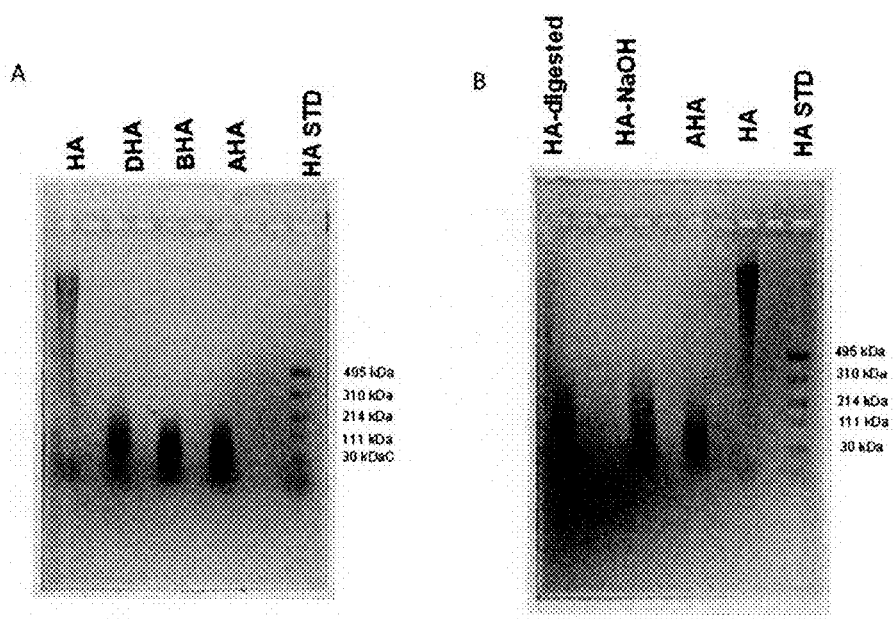
FIGS. 16 (A and B) shows two agarose gels comparing the sizes of derivatives obtained by hydrozenolysis and NaOH digestion of hyaluronic acid.

Table 1 shows the ratio of the free amino group to the glucuronic acid group. Re-acylation with acetic anhydride or butyric anhydride increased with increases in concentration of the acyl anhydride used Example 5: Deacetylation of HA Using Different Methods FIG. 16 shows the comparison of HA deacetylated for 72 hours using the hydrazinolysis reaction (DHA) and HA where NaOH was used as the deacetylating agent (DHA-NaOH). 2 g of HA was dissolved in 200 mL of 2.5N NaOH and the solution was stirred at room temperature for 72 hours. Water (140 mL) was added to the reaction mixture and stirred in an ice bath while the pH of the solution was adjusted to 10.0 with concentrated HCl, followed by precipitation in 800 mL of a 7:1 acetone-$H_2O$ mixture at 0° C. The white fibrous precipitate formed was recovered by filtration and dissolved in water and the pH was adjusted to 7.0. After evaporating the acetone in a rotary evaporator, the solution was lyophilized. The polymer was re-dissolved in water, dissolved salt was removed by dialysis and the sample was re-lyophilized. In FIG. 16 (A) HA, DHA, BHA, AHA and Select-HA LoLadder were run on a 0.75% w/v agarose gel in TAE running buffer, at a constant voltage of 100V for 1 hr and then visualized with 0.005% w/v "Stains-All". In FIG. 16B (B) HA digested, AHA-NaOH, AHA, HA and Select-HA LoLadder were run on a 0.75% w/v agarose gel.

DISCUSSION

It is apparent that with the NaOH treatment there was glycosidic bond cleavage of the initial HA chain (molecular weight of 1500-1800 kDa) causing a reduction of the molecular weight to 30-214 kDa, as estimated by agarose gel electrophoresis (FIG. 16 A). The re-acylation reaction had no significant effect on the molecular weight range of the polymers. The molecular weight range of AHA is similar to the molecular weight of HA-digested and AHA-NaOH (FIG. 16 B) under the conditions used.

Figure 17:
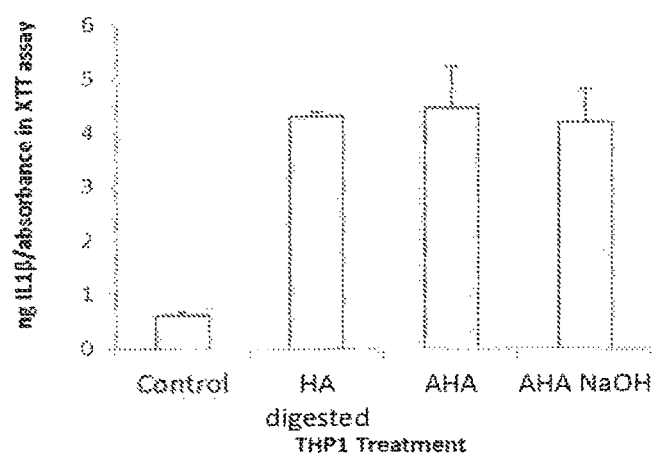
FIG. 17 shows the degree of stimulation of IL-1β by HA derivatives.

As shown in FIG. 17, the degree of IL-1β stimulation by AHA is comparable to that seen by LMHA obtained by digesting HA with bovine testicular hyaluronidase (HA-digested) and LMHA obtained by deacetylating HA with NaOH and re-acetylating with acetic anhydride (AHA-NaOH).

Figure 18:
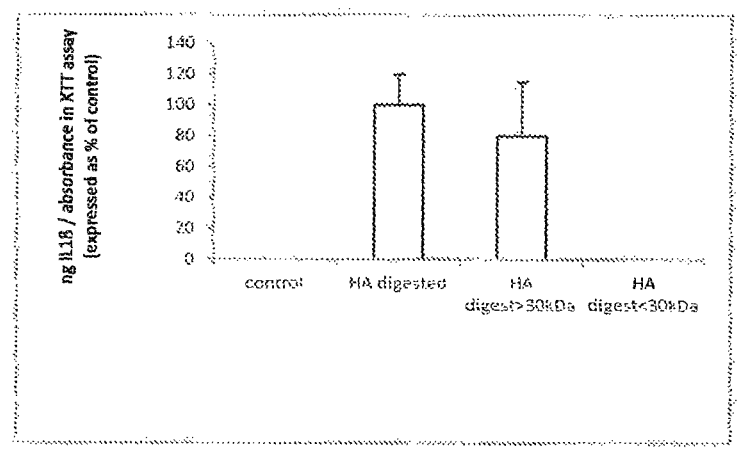
FIG. 18 shows the degree of stimulation of IL-1β of different molecular weights of HA derivatives.

FIG. 18 shows that digested hyaluronic acid, which is smaller than 30 kDa does not stimulate THP-1 IL-1ß secretion, used at a concentration equal to that of the unfractionated hyaluronic acid preparations of AHA (12.5 µg/mL). All of the stimulatory activity for IL-1ß secretion was in the fractions greater than 30 kDa, which were obtained by digesting the HA by the methods of treatment with testicular hyaluronidase, or hydrazinolysis or NaOH. The fractionation was carried out by PES gel filtration spin columns with a cut off of 30 kDa.

Figure 19:
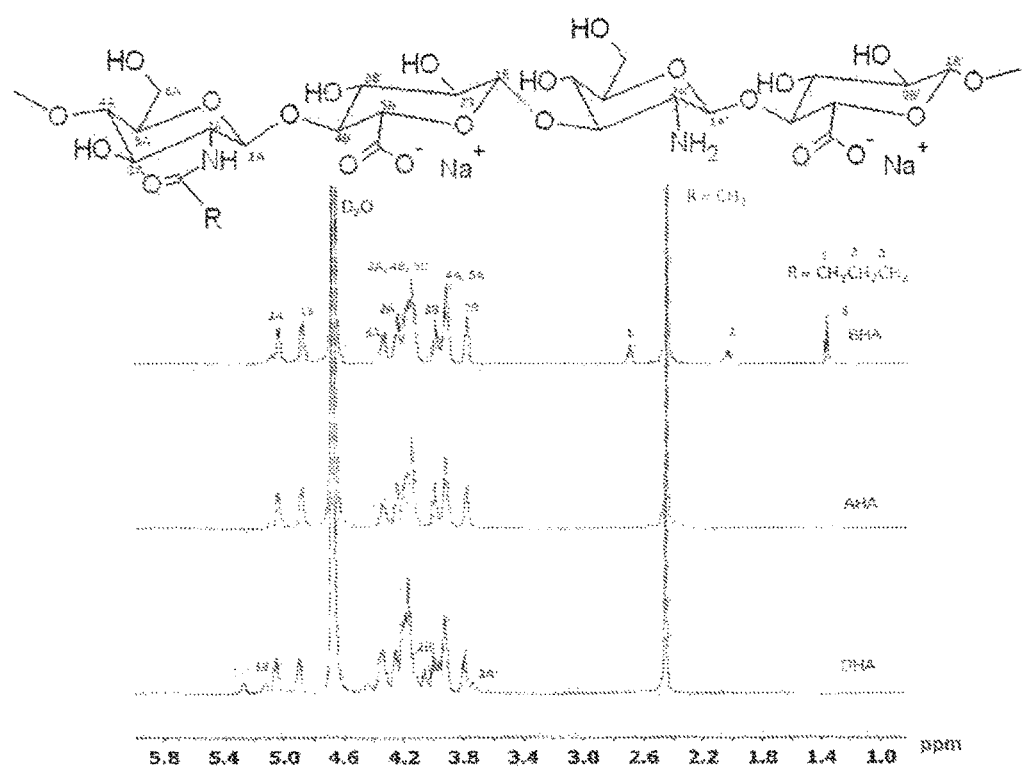
FIG. 19 illustrates the $^1$H-NMR spectra for the re-acylation of HA polymers.

Example 6: Nuclear Magnetic Resonance Spectroscopy of Re-Acylated Hyaluronic Acid Polymers FIG. 19 shows the $^1$H-NMR spectra for the re-acylated polymers. For HA deacetylated via the hydrazinolysis reaction, several N-acyl derivatives were synthesized using the appropriate anhydride. The $^1$H-NMR spectra of AHA, BHA and DHA in $D_2O$ confirmed the expected major peaks associated with the polymers' backbone. Table 2 shows the percentage of glucosamine, N-acetyl-glucosamine and N-butyryl glucosamine composition of AHA, BHA and DHA as calculated from $^1$H NMR spectrum.

Example 7: Characterization of Re-Acylated Polymers by Mass Spectroscopy

Mass Spectrometry was performed as following. Three mL of HA (5 mg/mL) was digested with 1 ml of 800-2000 units/mL of bovine testes hyaluronidase incubated at 37° C. for 24 hours. For HA derivatives, 500 µL of 30 mg/mL were digested with 1 ml of 800-2000 units/mL of bovine testes hyaluronidase. The enzyme was precipitated by boiling for 5 minutes and centrifuged at 2050 rpm for 10 minutes. The supernatant was collected and separated with a micron centrifugal filter device (Millipore Corporation) with a molecular weight cut-off of 3000 Da. The filtrate obtained from this digestion was lyophilized and used for the MS analyses. MS and MS/MS analyses were performed on a QSTAR XL hybrid quadrupole/time-of-flight (QqTOF) tandem mass spectrometer (Applied Biosystems/MDS SCIEX) equipped with Electrospray Ionization (ESI) source and was further confirmed using Thermo LTQ Orbitrap Velos Pro with Heated Electrospray ionization (HESI) source under negative mode. For ESI analysis under negative mode, the following source conditions were used: a curtain-gas setting of 25 and an ionspray voltage of −4000 V, Q0 declustering potential of −90 V, and a focusing potential −350 V. Nitrogen was used as the collision gas (CAD setting 5) for both TOF MS and MS/MS scans As shown in Table 2, digestion of HA and its derivatives by testicular hyaluronidase, an endo-β-N-acetylhexosaminidase yielded a homologous series of oligosaccharides having repeating units of (4GlcUAβ1-3GlcNAcβ1-). The oligosaccharides obtained were separated with micron centrifugal filter device with molecular weight cut-off of 3000 Da. The observed M/Z is very similar to the predicted M/Z as shown. The ion-spray mass spectra of the filtrate produced singly charged disaccharides (396.1159) and singly (797.2095) and doubly charged (387.1104) tetrassaccharides as a result of sodium abstraction. The number of charged ions observed corresponds to the number of glucuronic acid sodium salt moieties contained in the oligosaccharides. In addition to the molecular ions generated by the enzymatic degradation of AHA and DHA, the spectra generated by BHA showed additional molecular ions that coincide with singly charged disaccharides of N-butyryl glucosamine (GlcNBU) and GlcUA (424.1473), singly (853.2743) and doubly (415.1405) charged tetrassaccharides of GlcNBU and GlcUA and singly (825.2433) and doubly (401.1260) charged tetrassaccharides of GlcNBU, GlcNAC and GlcUA (4GlcUAβ1-3GlcNAcβ1-4GlcUAβ1-3GlcNBUβ1). This further confirms the $^1$HNMR spectra that the glucosamine moieties in DHA were successfully N-butyrylated (BHA).

Example 8: Identification of Cell Surface Receptor for N-Butyrylated Hyaluronic Acid (BHA)

Figure 20:
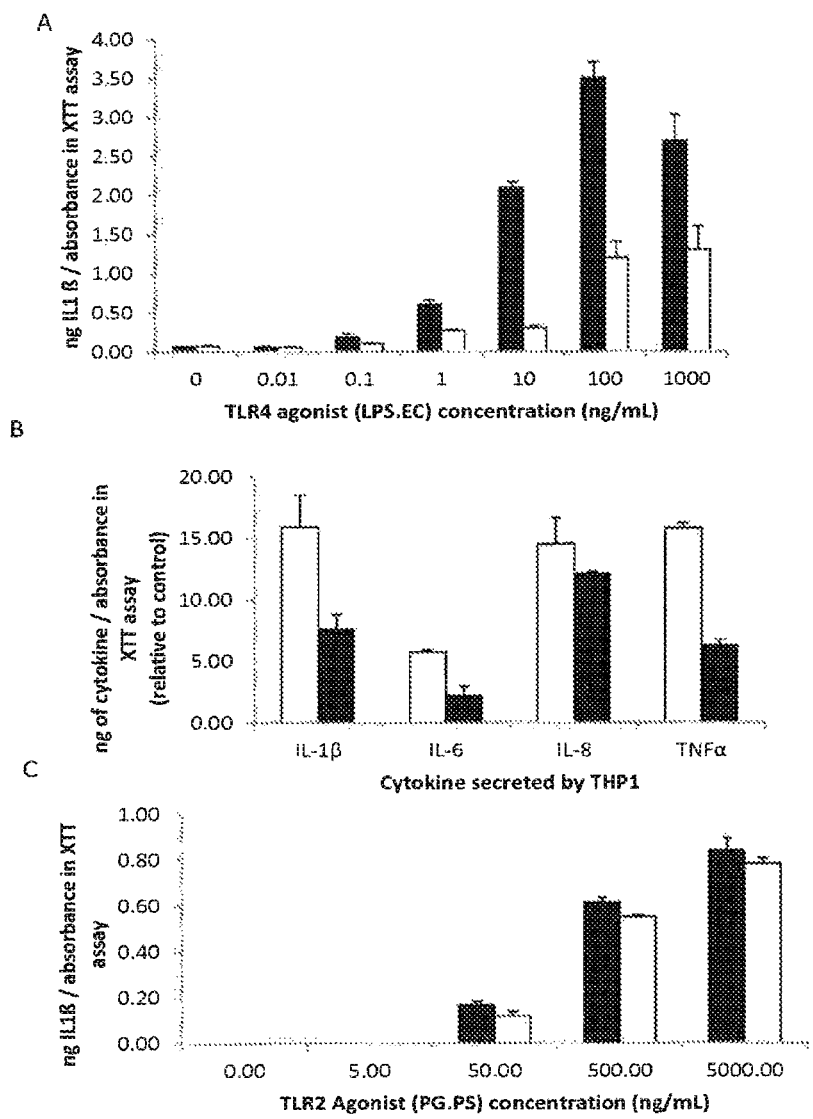
FIG. 20 (A,B,C) illustrates the identification of the cell surface receptor for an HA derivative.

FIG. 20A shows THP-1 macrophages were treated with increasing concentrations of the TLR-4 agonist (LPS-EC), with (□) or without (■) 500 µg/ml BHA and THP-1 and IL-1ß secretion measured. The IL-1β production by THP-1 cells was inhibited when co-incubated with 500 µg/ml of BHA at the various concentrations of TLR-4 shown. BHA inhibition of the AHA-dependent stimulation of IL-1β secretion was present between 0.1-1000 ng/ml ($p<0.05$, Student t-test). FIG. 20B shows the THP-1 cytokine secretion when treated with AHA in the presence and absence of BHA. THP-1 are untreated, or treated with either 500 µg/mL AHA only, (□), or 500 µg/mL BHA with 500 µg/mL AHA (■). The cytokine levels are expressed relative to untreated (THP-1 that is not treated with either AHA or BHA). The treatment of THP-1 with 500 µg/ml of AHA stimulated the secretion of IL-1β, IL6, IL8 and TNF-α which was inhibited when co-incubated with 500 µg/ml of BHA.

As shown in FIG. 20C, BHA probably does not act through the TLR-2 receptor. THP-1 are incubated with increasing concentrations of the TLR-2 agonist, PG.PS, In the presence (□) and absence (■) of 500 µg/mL BHA and these treatments are not statistically different. Overall, the data suggests that BHA exerts its anti-inflammatory effect through TLR-4.

Example 9: Cross-Linking of N-Acylated Hyaluronic Acid Derivatives with Genipin

Deacetylation of HA:

To form the partially de-acetylated HA using the hydrazinolysis reaction, 3 g of HA was dissolved in 150 ml of hydrazine monohydrate and 1.5 g of hydrazine sulphate at 55'C for 48 (DHA48) and 144 hours (DHA144) hours. The polymeric product was precipitated, washed with ethanol and dried at 25'C for 24 hours. The sample was dissolved in a mixture of 50 ml of 5% v/v acetic acid and 30 mL of 0.5M iodic acid and kept in a bath at 4'C for at least one hour. 8.75 mL of aqueous 57% v/v $CH_3I$ was added and stirred for 15 minutes. The deep violet colour of the solution was removed via liquid—liquid extraction with ethyl ether. The pH of the aqueous layer, containing the deacetylated HA, was adjusted to 7.0-7.5, precipitated with ethanol. The polymer was dissolved in water, dialyzed against double distilled $H_2O$ and freeze dried.

Butyrylation of DHA144:

DHA144 was butyrylated with 1% butyric anhydride in absolute ethanol (BHA144) according to the method used for N-propionylation of the glucosamine monomer. Briefly, 0.1 g of DHA144 dissolved in 30 ml of distilled water and 6 mL of saturated $NaHCO_3$ was added. 60 uL of butyric anhydride was added to 5.94 mL of absolute alcohol and added to the reaction mixture. The reaction mixture was stirred for 10 minutes and then quenched in a boiling water bath for 5 minutes. Residual ethanol was evaporated by using the rotary evaporator and then the sample lyophilized to remove the water. The lyophilized sample was dialyzed against distilled water using dialysis tubing with molecular weight cut off of 6000 and re-lyophilized.

Characterization of Polymers

Colorimetric Assay.

To quantify the extent of deacetylation of HA with time and to quantify the unmodified glucosamine moiety in the BHA144 sample, colorimetric quantification of the glucosamine and glucuronic content of the polymer was determined. The glucosamine content based on the derivatization reaction of its primary amino group (from glucosamine) with o-phthaldehyde and the thiol group of N-acetyl-L-cysteine. The glucuronic content was quantified according to the carbazole reaction. Results were expressed as the molar ratio of glucosamine to glucuronic acid.

Molecular Weight Estimation:

The molecular weight range of the samples was estimated by electrophoresis of HA on a 0.75% w/v agarose gel cast and run in TAE buffer (pH 8.0) at 100V for 90 minutes. The bromophenol blue tracking dye migrated close to the end of the gel during this time period. Immediately after the run, the gel was placed in approximately 100 ml of solution containing 0.005% w/v Stains-All in 50% v/v ethanol overnight in the dark at room temperature. For destaining, the gel was transferred to 10% v/v ethanol solution and stored in the dark for one day with two or more changes of destaining solution.

Gelation Time:

The polymers were dissolved in 0.1M PBS solution at pH of 7.4 at a concentration of 40 mg/ml. Genipin was dissolved in 0.1M PBS solution at pH 7.4 at a concentration of 30 mM. The genipin solution was left to dissolve at room temperature for 1 week. 30 mM genipin solution was further diluted to 15 mM and 7.5 mM with 0.1M PBS solution. 300 µL of 40 mg/ml of polymers was added to 300 µL of 30 mM, 15 mM and 7.5 mM genipin solution and allowed to react at 37° C. for 2 hours. For some experiments, type I collagen was mixed with the DHA48 solution at a ratio of 20:80, which resulted in a weight ratio of 1:20. Total loading of genipin in the sample were 0.34, 0.17 and 0.085% w/v respectively while the total loading of the polymers was 2% w/v.

The sample was transferred to the rheometer to determine the gelation time. The rheometer used was a TA Instruments AR 2000™ rheometer (TA Instruments, New Castle, Del.) equipped with a cone-and-plate fixture consisting of a 0.5 DEG, 4 cm diameter stainless steel cone. To prevent drying of the samples during experiments, a steel ring of approximately 6 cm in diameter was placed around the measuring geometry. The in situ gelation of behavior of the hydrogel was studied in the time sweep mode at a constant frequency of 1 Hz, constant temperature of 37° C., constant pressure of 20 Pa and physiological pH of 7.4. This study enabled the monitoring of the evolution of viscoelastic properties such as elastic stored modulus G' and the viscous loss modulus (G") with time. The dynamics of both viscoelastic characteristic functions were used to determine the gelation time which is approximated as the instant at which G" intersect G.

Results:

Deacetylation.

Figure 21:
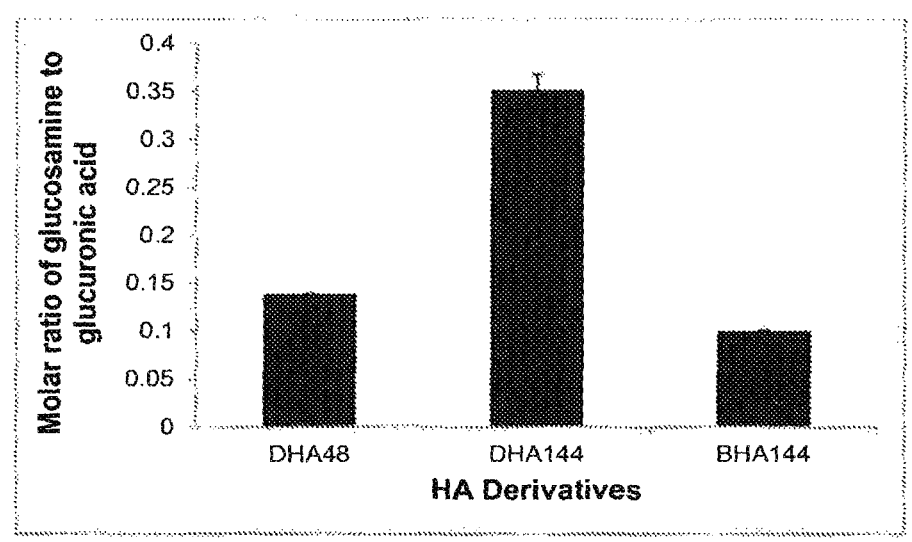
FIG. 21 shows the molar ratio of glucosamine to uronic acid for cross-linked hyaluronic acid derivatives.

Some of the GlcNAc units of HA were converted to glucosamine via the hydrazinolysis reaction at 55° C. for 48 and 144 hours. FIG. 21 shows the molar ratio of glucosamine to glucuronic acid versus increasing reaction time, the molecular weight range of the polymer decreased, while the molar ratio of glucosamine to glucuronic acid increased from 0.138±0.001 for DHA48 to 0.351±0.017 for DHA144 as determined by the colorimetric assay. When DHA144 was reacted with 1% butyric anhydride for 10 minutes to form BHA144, their molecular weight range remained the same, however, the ratio of glucosamine to glucuronic acid in DHA144 (0.351±0.017) decreased to 0.099±0.002 when reacted ratio 1% butyric anhydride.

Gelation Time.

Figure 22:
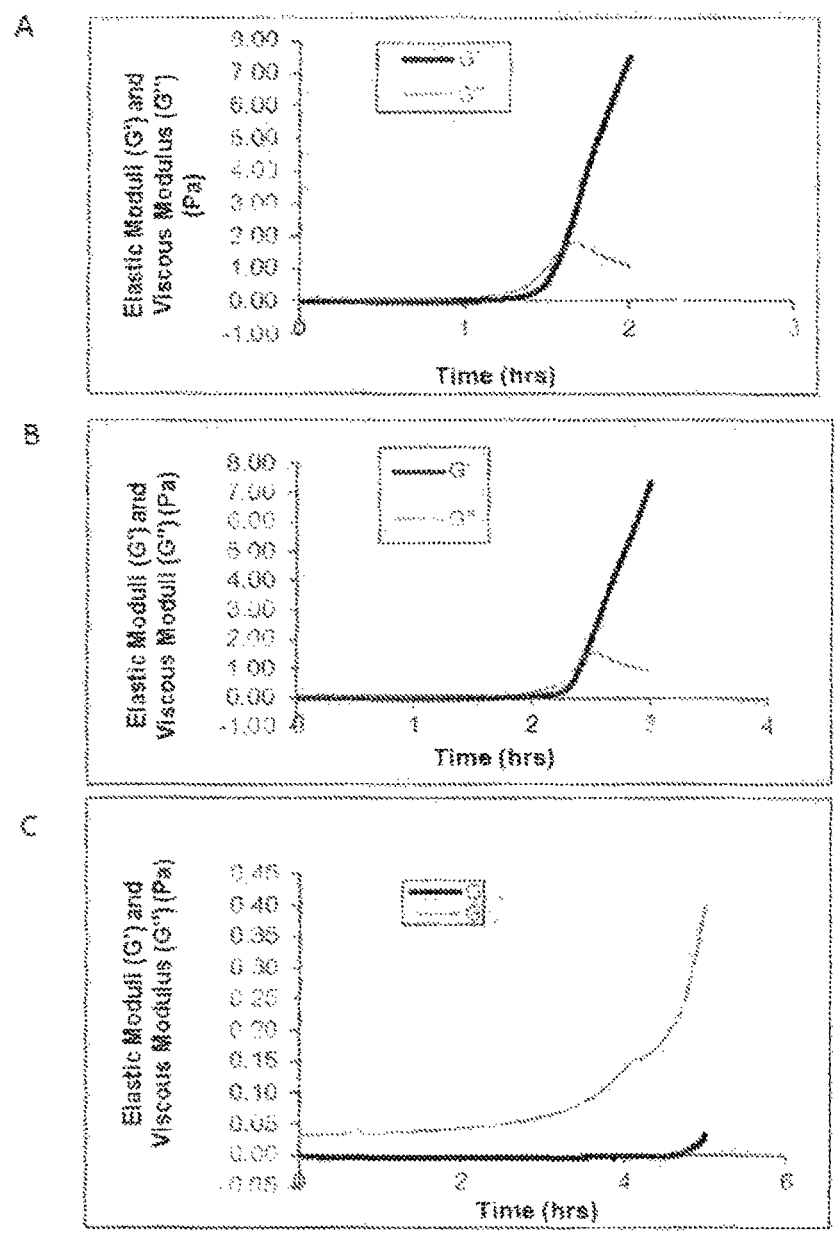
FIG. 22 illustrates the dynamics of the elastic and viscous moduli dynamics for different concentrations cross-linked the hyaluronic acid derivatives.

To determine the gelation kinetics and the gel properties, the rheological behavior such as G" and G' were monitored. The gelation time was based on the intersection of G' and G". FIGS. 22a, 22b and 22c shows the time sweep profiles of G' and G" near the gel point for DHA48 with 0.34, 0.17 and 0.085% w/v genipin loading. FIG. 22a shows the time sweep profiles of G' and G" near the gel point for DHA144 cross linked with 0.34% w/v genipin loading, while FIGS. 22b and 22c shows the time sweep profiles of G' and G" near the gel point for BHA144 crosslinked with 0.34 and 0.17% w/v genipin loading. For the samples, initially, G" was larger in value than G', which was expected since the samples were still in the liquid state and thus the viscous property was dominant at that point. With time, both G' and G" increased as the solution began to become gel-like due to the formation of crosslinked network. At this point, the rate of increase of G' became higher than G" because the elastic properties became dominant. The difference in rate of increase of G' and G" led to their crossover. The time required to achieve this crossover is the gelation time. For FIG. 22, the dynamics, if elastic (G') and viscous (G") moduli near the gel point at 1 HZ (A) DHA48 crosslinked, are for (A) 0.34 w/v % genipin; for (B) 0.17 w/v % genipin; and for (C) 0.085 w/v % genipin.

Table 3 shows the gelation time for each of the samples and conditions tested. For the DHA48 sample with 0.34% w/v loading of genipin sample exhibited a gelation time of 1.6 hrs, while the sample with 0.17% w/v loading of genipin exhibited a gelation time of 2.4 hours. On the other hand, the sample with 0.085% w/v loading of genipin did not reach gel point after 5 hours of testing. These results indicate that the gelation time is inversely proportional to the genipin concentration.

TABLE 1

MOLECULAR WEIGHT OF HYALURONIC ACID AND DERIVATIVES

| Sample | Mol wt range (kDa) |
|---|---|
| HAo | 214->495 |
| HA1 | 310->495 |
| HA2 | 310->495 |
| HA3 | 214->495 |
| DHAo | <30-495 |
| DHA1 | <30-495 |
| DHA2 | <30-310 |
| DHA3 | <30-310 |
| AHAo | <30-495 |
| AHA1 | <30-495 |
| AHA2 | 30-214 |
| AHA3 | <30-495 |
| BHAo | <30-495 |
| BHA1 | <30-495 |
| BHA2 | <30-310 |
| BHA3 | <30-310 |

TABLE 2

The percentage of —$NH_2$, N-acetyl and N-butyryl moieties in DHA, AHA and BHA as calculated from $^1$H NMR Spectra.

| Sample | Molar ratio free amino group (glucosamine): glucuronic acid | Glucosamine (%) | N-Acetyl-Glucosamine (%) | N-Butyryl-Glucosamine (%) |
|---|---|---|---|---|
| DHA | 0.2200 ± 0.0100 | 19.7 ± 3.5 | 82.8 ± 3.1 | — |
| AHA | 0.0044 ± 0.0005 | — | 98.7 ± 1.5 | — |
| BHA | 0.0040 ± 0.0010 | — | 82.2 ± 4.6 | 22.7 ± 3.8 |

TABLE 3

Observed molecular ion species in AHA, BHA and DHA and their relative intensities.

| Molecular ions | Charge | Predicted M/Z | Observed M/Z AHA | Observed M/Z BHA | Observed M/Z DHA |
|---|---|---|---|---|---|
| Dissaccharide of GlcNAC and GlcUA | −1 | 396.1142 | 396.1158 (31) | 396.1159 (28) | 396.1156 (28) |
| Tetrasaccharide of GlcNAC and GlcUA | −1 | 797.2076 | 797.2092 (22) | 797.2095 (12) | 797.2098 (9) |
| Tetrasaccharide of GlcNAC and GlcUA | −2 | 387.1095 | 387.1104 (100) | 387.1104 (100) | 387.1102 (100) |
| Dissaccharide of GlcNBU and GlcUA | −1 | 424.1455 | — | 424.1473 (2) | — |

TABLE 3-continued

Observed molecular ion species in AHA, BHA and DHA and their relative intensities.

| Molecular ions | Charge | Predicted M/Z | Observed M/Z AHA | Observed M/Z BHA | Observed M/Z DHA |
|---|---|---|---|---|---|
| Tetrasaccharide of GlcNBu and GlcUA | −1 | 853.2708 | — | 853.2743 (0.3) | — |
| Tetrasaccharide of GlcNBu and GlcUA | −2 | 415.1408 | | 415.1419 (3) | |
| Tetrasaccharide of GlcNAC, GlcNBU and GlcUA | −1 | 825.2395 | — | 825.2433 (2) | — |
| Tetrasaccharide of GlcNAC, GlcNBU and GlcUA | −2 | 401.1251 | — | 401.1259 (36) | — |

TABLE 4

Gelation time

| Sample | Loading of genipin (% w/v) | Gelation Time (hrs) |
|---|---|---|
| DHA48 | 0.340 | 1.60 |
| DHA48 | 0.170 | 2.40 |
| DHA48 | 0.085 | * |
| DHA144 | 0.340 | 2.90 |
| DHA144 | 0.170 | — |
| BHA144 | 0.340 | 2.50 |
| BHA144 | 0.170 | 2.55 |
| Col20DHA80 | 0.340 | 1.45 |
| Col20DHA80 | 0.170 | 2.88 |

* did not gel after 5 hours of testing
Col = type 1 collagen.

The invention claimed is:

1. A pharmaceutical composition for treating skin inflammation, comprising: a pharmaceutically acceptable excipient or carrier, and a therapeutically effective amount of a hyaluronic acid derivative comprising repeating units of a disaccharide of Formula (I), wherein a portion of the disaccharide units of Formula (I) have been independently replaced with a disaccharide structure of Formula (II) wherein R is —C(O)—($C_2$-$C_4$)-alkyl, or a pharmaceutically acceptable sodium- or potassium-salt, ester or glucoside thereof,

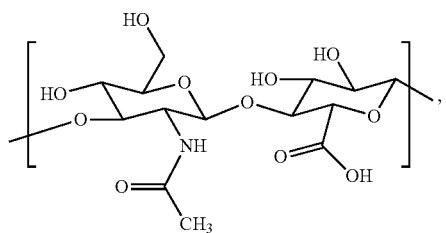

(I)

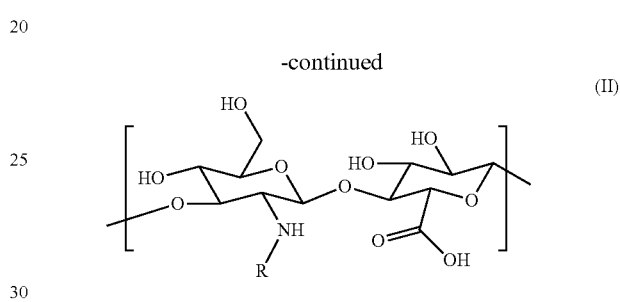

(II)

wherein the hyaluronic acid derivative has a molecular weight of at least about 20 kDa, and wherein the hyaluronic acid derivative reduces production of inflammatory cytokines whereby when applied to skin, skin inflammation is treated, and wherein treating skin inflammation comprises treating loss of substance of the skin.

2. The pharmaceutical composition according to claim 1, wherein the loss of substance of the skin is due to medical or cosmetic reasons.

3. A method for the treatment of psoriasis or an inflammatory condition of the skin, comprising administering to a patient in need thereof a hyaluronic acid comprising repeating units of a disaccharide comprising glucuronic acid and N-acetylglucosamine, wherein a portion of the N-acetyl groups of the N-acetylglucosamine have been independently replaced with a group of the formula —N—C(O)—($C_2$-$C_4$)-alkyl, and wherein the hyaluronic acid derivative has a molecular weight of at least about 20 kDa, or a pharmaceutically acceptable sodium or potassium salt, ester, or glucoside thereof.

4. The method of claim 3, wherein the inflammatory condition of the skin results from production of pro-inflammatory cytokines in the patient.

5. The method of claim 3, wherein the inflammatory condition of the skin results from loss of substance of the skin.

6. The method of claim 5, wherein the loss of substance of the skin is due to medical or cosmetic reasons.

* * * * *